United States Patent [19]
Kenney

[11] Patent Number: 6,064,912
[45] Date of Patent: May 16, 2000

[54] ORTHOTIC/ELECTROTHERAPY FOR TREATING CONTRACTURES DUE TO IMMOBILITY

[76] Inventor: John P. Kenney, 28571 Bella Vista, Laguna Niguel, Calif. 92677

[21] Appl. No.: 09/048,324

[22] Filed: Mar. 25, 1998

Related U.S. Application Data

[63] Continuation-in-part of application No. 08/827,604, Mar. 28, 1997, Pat. No. 5,891,068.

[51] Int. Cl.[7] .................................................. A61N 1/08
[52] U.S. Cl. .............................. 607/48; 602/5; 602/20; 602/23; 602/16
[58] Field of Search ......................... 602/20, 23, 26, 602/16, 1; 607/48, 49, 77, 149, 98, 108–111, 112, 114; 601/23, 33

[56] References Cited

U.S. PATENT DOCUMENTS

| | | |
|---|---|---|
| 4,433,679 | 2/1984 | Mauldin et al. . |
| 4,595,010 | 6/1986 | Radke ........................................ 128/421 |
| 4,779,629 | 10/1988 | West et al. . |
| 4,817,588 | 4/1989 | Bledsoe . |
| 4,846,842 | 7/1989 | Connolly et al. . |
| 4,865,024 | 9/1989 | Hensley et al. . |
| 4,982,732 | 1/1991 | Morris . |
| 5,036,837 | 8/1991 | Mitchell et al. . |
| 5,052,379 | 10/1991 | Airy et al. . |
| 5,054,476 | 10/1991 | Petrofsky et al. ........................ 602/16 |
| 5,116,296 | 5/1992 | Watkins et al. . |
| 5,121,747 | 6/1992 | Andrews ............................... 602/16 X |
| 5,188,584 | 2/1993 | Petrofsky et al. ........................ 602/16 |
| 5,437,619 | 8/1995 | Malewicz et al. ........................ 602/20 |
| 5,437,811 | 8/1995 | Stern . |
| 5,558,627 | 9/1996 | Singer et al. ........................ 602/16 X |
| 5,628,722 | 5/1997 | Solomonow et al. .................... 602/26 |
| 5,685,830 | 11/1997 | Bonutti . |

Primary Examiner—Richard J. Apley
Assistant Examiner—Jayne Saydah
Attorney, Agent, or Firm—Stout, Uxa, Buyan & Mullins; Frank J. Uxa

[57] ABSTRACT

A therapeutic system comprising an orthotic device adapted to extend the range of angular movement between adjacent first and second skeletal body parts which have been drawn to and involuntarily held in a limited angular range of motion position relative to one another by contraction of muscle fibers and connective tissue due to immobility of one or both of said skeletal body parts and an electrode component positioned to be effective to conduct an electrical current to at least one of said body parts.

6 Claims, 14 Drawing Sheets

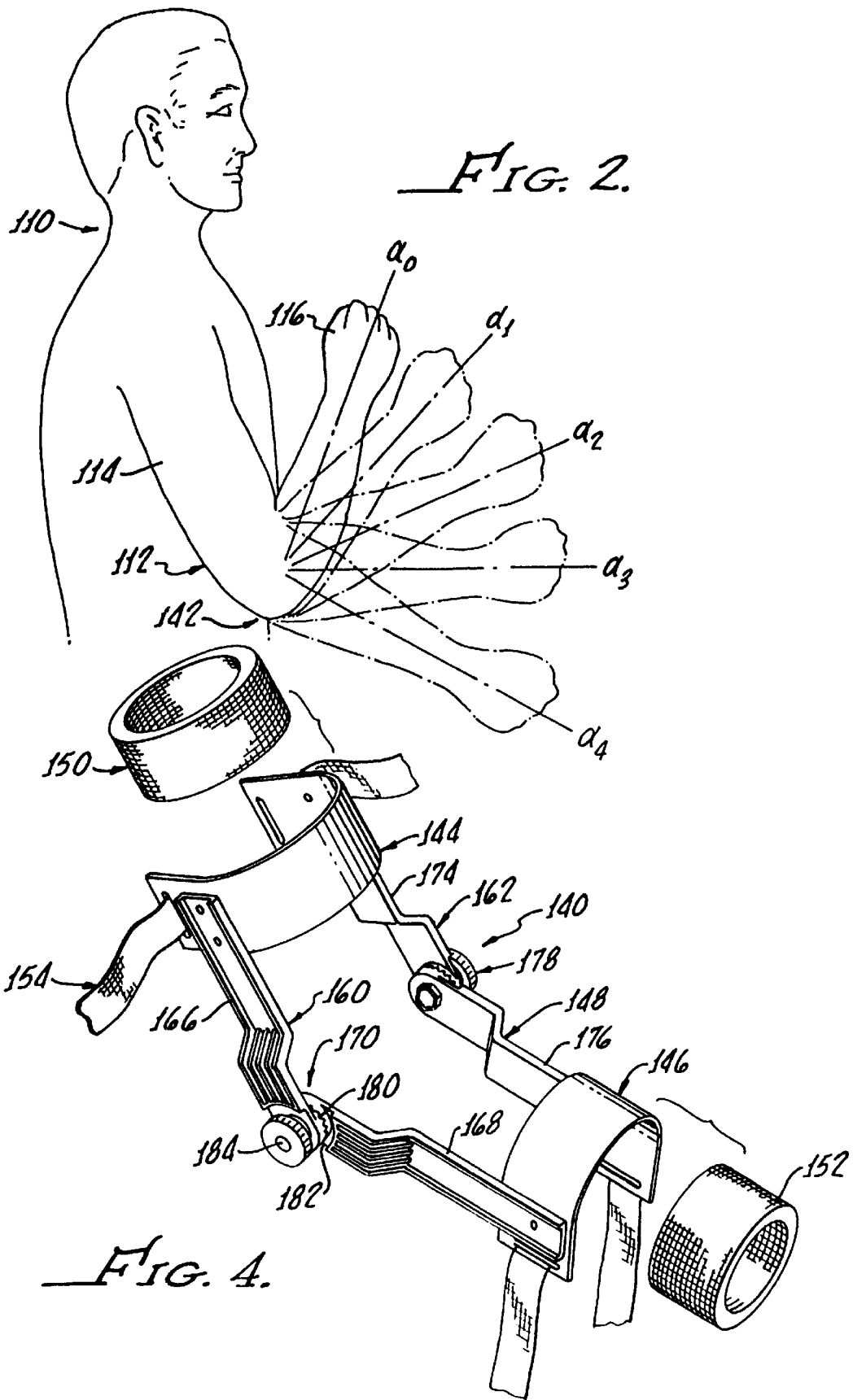

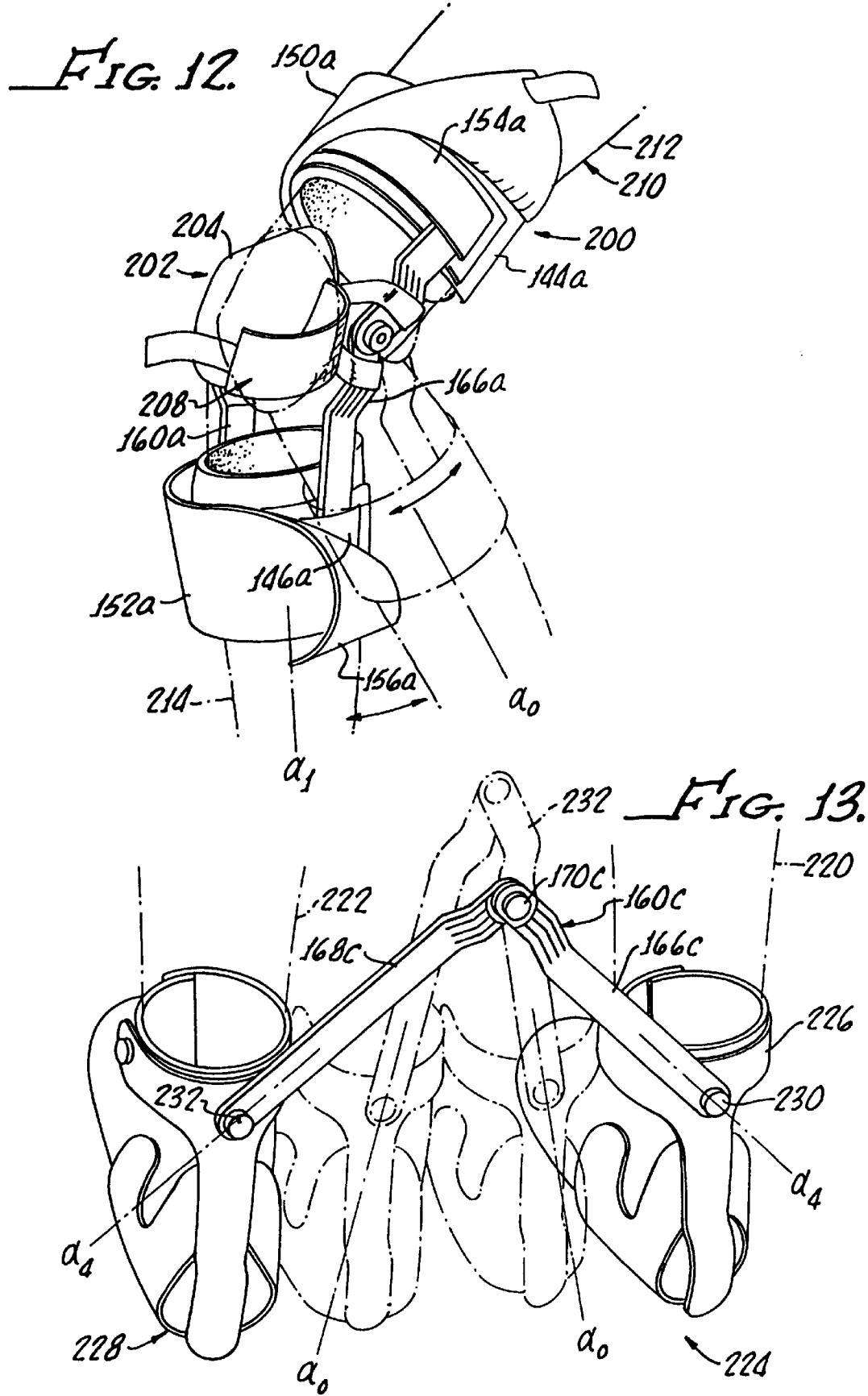

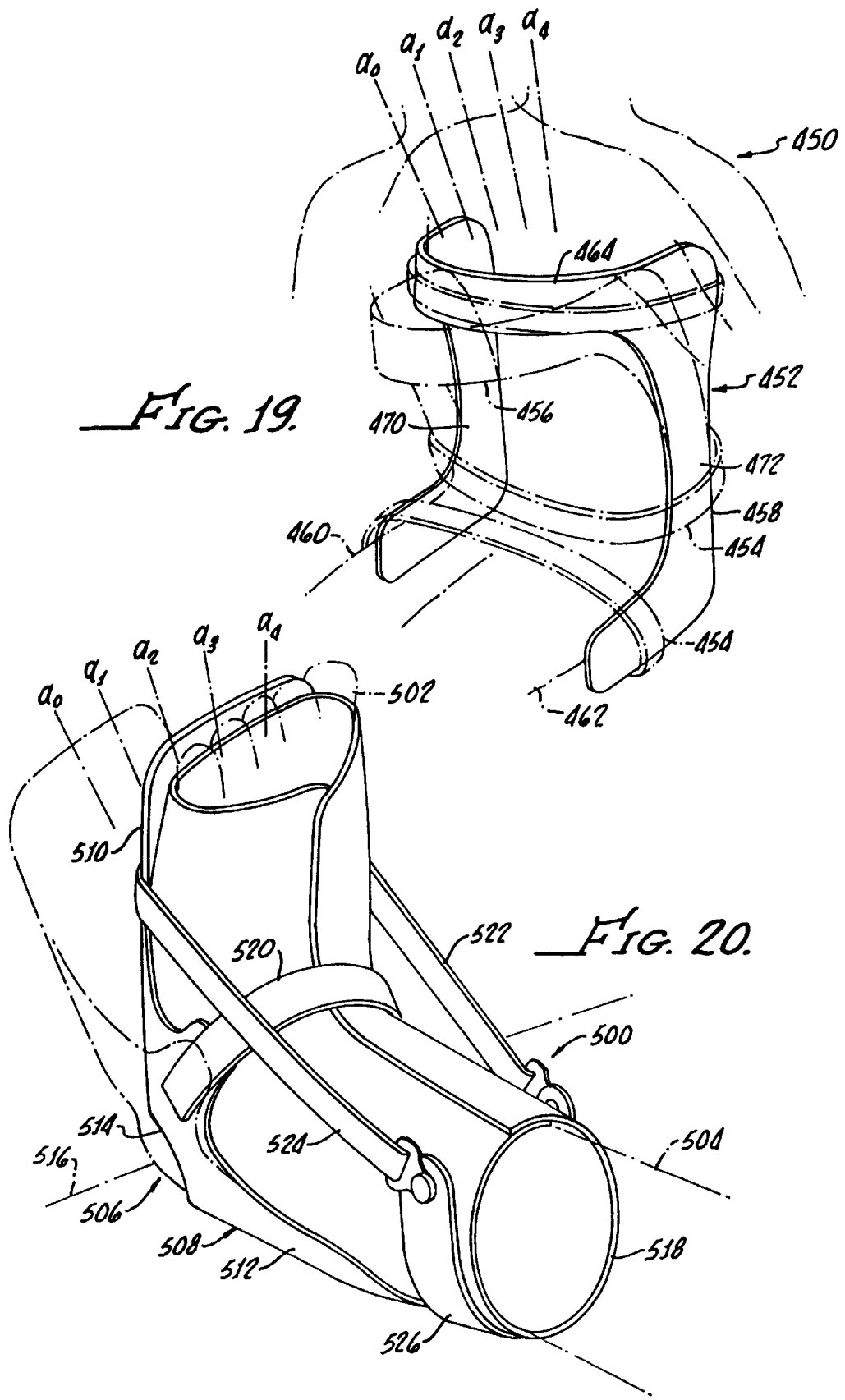

ORTHOTIC/ELECTROTHERAPY FOR TREATING CONTRACTURES DUE TO IMMOBILITY

RELATED APPLICATION

This is a continuation-in-part of application Ser. No. 08/827,604 filed Mar. 28, 1997, now U.S. Pat. No. 5,891,068 the disclosure of which is incorporated in its entirety herein by reference.

BACKGROUND OF THE INVENTION

1. Field of Invention

The present invention relates generally to the field of orthotic devices and appliances; more particularly to orthotic devices and appliances in combination with electrotherapy useful for restoring movement to a connective joint of a mammalian body; and still more particularly to orthotic devices and appliances in combination with electrotherapy used to reverse contractures due to immobility and neurological dysfunction.

2. Background Discussion

Webster's New Collegiate Dictionary defines "orthotics" as "a branch of mechanical and medical science that deals with the support and bracing of weak or ineffective joints or muscles."

Orthotic devices and appliances, commonly referred to just as "orthotics" (in spite of the broader dictionary definition of orthotics) have been utilized for many years by physical therapists, occupational therapists, and certified orthotic fitters to assist in the rehabilitation of loss of range of motion (LROM) of patients' joints and associated limbs or adjacent skeletal parts of the patients' body.

Orthotics, as well as splints, have been designed both to maintain and to restore the range of bodily motion due to LROM. Such loss of range of motion may, for example, be caused by traumatic injury, rehabilitation following joint or limb surgery, and contracture due to immobilization caused by neuromuscular disorders (e.g., stroke and closed head injury) and other disease processes that significantly limit a patient's ability to use a joint for normal activities of daily living (ADL).

Two fundamentally different types of contractures exist which clinically should have two different treatment protocols. The difference in these two types of contractures is the basis for the clinical techniques and design of the orthotics of the present invention which will be described below.

A first one of these two fundamentally different types of contracture may be defined as a fixed, high resistance of muscle to passive stretch resulting from fibrosis of the muscles and joints, or from disorders of the muscle fiber resulting in LROM, for example, of a patient's arm or leg. In this regard, Webster's Dictionary defines "contracture" as "a permanent shortening (as of muscle, tendon and scar tissue) producing deformity or distortion."

This first type of contracture is usually due to trauma, injury, or surgical intervention affecting the joint, as may be typical of sports injuries and the treatment thereof. As the injured tissue heals, edema, post trauma or surgically affected tissue regeneration and other natural healing processes result in fusing together of what were, prior to the trauma, separate, pristine connective tissues, that is, the collagen fiber matrix (depicted diagrammatically in FIG. 1A hereof), capable of easily gliding over one another, as is needed for normal joint movement and related muscle elongation.

However, post-trauma, this collagen fiber matrix becomes random and irregular (depicted diagrammatically in FIG. 1B hereof), and neither elongates nor stretches compared to non-traumatized collagen fibers. This fusing-together or adhesion of connective tissue structures (e.g., ligaments, tendons, synovial membrane, fascia and fibrous joint capsules) is the result of the tissues being invaded by developing undifferentiated scar between adjacent tissue, thereby diminishing or preventing the mutual gliding after early healing of the trauma or post-surgical trauma has been accomplished.

Such fusing together of connective tissue is a leading cause of lags (a non-specific indictment of the motor system's failure to move the affected joint through the full available passive range) relating to tendon gliding, depending on their strategic placement in reference to structures crossing the joint. With limited mobility and associated extensor muscle atrophy, combined with the formation of adhesions and scar tissue in the form of a significantly increased number of joined fiber matrix junctions, the muscle fibers become shortened.

The restoration of full range of motion where fibrosis of the muscle fiber with scar tissue and adhesions are present, requires that the adhesions and scar tissue or fused fiber matrix junctions be "worked through" or broken to restore normal functional elongation or stretch. The term "no pain, no gain" (of increased ROM) is associated with the process of breaking through joined or fused fiber matrix junctions to restore full elongation of the connective tissue, tendons and muscles associated with the trauma-affected joint.

Heretofore known orthotics are primarily designed to treat this first type of contracture, but have also been used to treat contractures caused by immobility and neurological dysfunction (described below). However, such orthotic devices are not, as far as is known by the present inventor, best suited for such additional purpose.

The second and very different type of contracture results from joint immobility—not joint-related trauma or surgical repair of a joint. Contracture resulting from immobility is simply a shortening and thickening of the connective tissue, tendons and muscles (depicted in FIG. 1C hereof) that restrict the ROM of a joint. In such situations, the muscle fibers still retain their original uniform shape and there are no adhesions or scar tissue or significantly increased joined fiber matrix junctions to break through in order to restore full range of motion.

In contrast to trauma-caused contractures, contractures due to immobility do not need a "no pain, no gain" approach to restoring the normal range of motion, and, in fact, such an approach can actually do more harm than good. As mentioned above, the collagen fibers of a contracture due to immobility are simply shorter and thicker, and will respond to appropriate stretching techniques and motion of the joint to restore LROM. The stretching technique usually used for contractures caused by immobility is Range Of Motion (ROM) Therapy and the use of Low-Load Protracted Stretch/Stress (LLPS) or "extended stretch" static or dynamic orthotic devices.

According to authors Kenneth R. Flowers and Susan L. Michlovitz in their article titled "ASSESSMENT AND MANAGEMENT OF LOSS OF MOTION IN ORTHOPEDIC DYSFUNCTION" (published in Postgraduate Advances in PHYSICAL THERAPY, American Physical Therapy Association, 1988 II–VIII), Total End Range Time (TERT) in conjunction with LLPS is the key to restoring full ROM.

All contractures, whether caused by injury, surgery, or immobility, limit range of motion of the affected joint and make simple activities of daily living, such as eating and self-dressing, more difficult, if not impossible. Moderate to severe contractures can be debilitating, and can leave afflicted individuals bed-bound and unable to care for themselves in the most basic daily living tasks. Even mild contractures due to immobility can progress to severe contractures if proper intervention is not prescribed and implemented so long as the immobility continues.

Electrotherapy has been used extensively in the rehabilitation of joint and muscle related injury, pain, and LROM. Electrotherapy also has demonstrated other valuable healing properties. Many forms of electrotherapy exist, and are characterized by the wave form of the electrical current. The wave form "rate" or frequency refers to the number of pulses delivered per second. Pulse rate is the number of pulses in each energy wave. Pulse width is the length of time each energy burst stays on (for example, double pulse width to double the energy in that pulse). Pulse amplitude or height of the pulse increases as the amplitude setting is increased. The total energy per pulse is determined by the amplitude and pulse width. Many variations of electrotherapy wave forms exist that are utilized therapeutically for joint rehabilitation, pain management, and the healing properties provided by electrical stimulation.

The use of transcultaneous electric neuromuscular stimulation or TENS has been used extensively to treat muscle injury and related pain. TENS is characterized by biphasic electric current and selected parameters. TENS has clinically demonstrated the ability to increase blood flow, reduce swelling and edema, and provide both acute and chronic pain relief. TENS is commonly used to treat back and cervical muscular and disc syndromes, arthritis, shoulder syndromes, neuropathies and many other conditions. Neuromuscular electrical stimulation or NMES also provides many therapeutic benefits. NMES is characterized by a low volt stimulation targeted at motor nerves to cause a muscle contraction. Electrically controlled contraction/relaxation of muscles has been found to effectively treat a variety of musculoskeletal and vascular conditions. It is used to maintain or increase range of motion, prevent or retard disuse atrophy, muscle re-education, relaxation of muscle spasm, increase circulation, and for deep vein thrombosis prevention.

Microcurrent therapy is characterized by a subsensory current that acts on the body's naturally occurring electrical impulses to decrease pain and facilitate the healing process. Such form of electrotherapy provides symptomatic pain relief for both post surgical and post traumatic acute pain. Interferntial therapy or IF is characterized by the crossing of two medium, independent frequencies which work together to effectively stimulate large impulse fibers. These frequencies interfere with the transmission of pain message at the spinal chord level. Because of these frequencies, the IF wave meets low impedance when crossing the skin to underlying tissue. This deep tissue penetration can be adjusted to stimulate parasympathetic nerve fibers for increased blood flow and edema reduction. High Voltage Galvanic Therapy is characterized by high volt, pulsed galvanic stimulation, and used primarily for local edema reduction through muscle pumping and through "polarity effect". This type of electrotherapy is used to increase or maintain range of motion, to treat disuse atrophy, for muscle re-education, to increase circulation, and to treat degenerative joint disease.

Different electrotherapy wave forms, for example, as described above, have been identified for the treatment of varying conditions. Some of the benefits are perceptible to the user (felt during therapy) and others are below the perception level. The specific electric pulse width and pulse rate can be controlled and varied, and as a result can have a wide range of clinical benefits. Electrotherapy can elicit very significant muscle contraction of specific muscles to entire muscle groups. On the opposite end of the spectrum, electrotherapy can be used to inhibit muscle contraction and even provide total nerve block therapy simply by directing the correct electrical wave form to the appropriate site to have the desired clinical effect. Electrotherapy has also been used to keep neurotransmitters in the muscles functioning normally until new neuropathways can be developed to reconnect the muscle groups to the brain post stroke, spinal cord injury, closed head injury, etc.

Electrotherapy has also been used to provide soft tissue therapy, and has been used extensively for the repair of nerves, tendons and ligaments as well as muscles. IF and electro-therapeutic applications have been used to treat contractures, re-connect damaged neuro-pathways, heal chronic wounds, and to treat incontinence. The U.S. Public Health Department in it's pamphlet on The Treatment of Pressure Sores cited electrotherapy has having the greatest clinical promise of providing possible treatment breakthroughs in the treatment of chronic wounds.

Electrotherapy is applied primarily through the use of an electrotherapy unit (device emitting a controlled electrical wave form and amplitude) through electrical connections to strategically placed electrodes placed on the body to provide electrical current to the desired site.

A principal objective of my current invention is accordingly to provide more clinically effective orthotics that are an alternative to the known types of orthotics currently used to treat contractures caused by immobility and the ROM stretching technique. The main function of my new and more effective orthotic devices is to treat contracture due to immobility—not trauma related to surgery or injury.

The present inventor considers that TERT with Activity Stimulus strategy (i.e., flexing)—not LLPS—is the key to predisposing tissue to elongation and restoring range of motion, where LROM is due to immobility or neurological dysfunction.

The clinical importance and value of my invention are significant in that contractures and other hazards of immobility are one of the ten current highest health care costs in America that are totally preventable. This puts the health risks associated with immobility in the same category as cigarette smoking, alcohol and drug abuse, and automobile accidents in financial impact on American health care costs.

The new orthotic devices of the present invention provide more effective clinical treatment for LROM due to immobility by increasing the "stimulus of activity" of the affected tissue (connective and muscle fiber) rather than just holding the issue in moderately lengthened position (LLPS or "gradual extension" therapy). According to Brand (1984), "It is better not to use the word stretch for what should be long-term growth. If we want to restore normal length to a tissue that has shortened after disease (or disuse), we need to reverse the process and apply the stimulus of activity, or better, the stimulus of holding the tissue in the moderately lengthened position for a significant time." According to Brand, it will then "grow" or lengthen. Flowers and Michovitz in the before-mentioned article theorize that the joint somehow senses or computes the total stress applied to it in any given direction over a period of time. It then stimulates a proportionate amount of biological activity, leading to a proportionate mount of remodeling of the stressed tissue. The total stress is a product of its intensity, frequency and duration. The crucial elements in this conceptual model are frequency and duration. Total stress equals intensity times frequency times duration (intensity×frequency×duration).

The present orthotic devices increase the stimulus of activity relative to current orthotic devices which simply hold the limb and joint in an extended position for extended periods. Conceptually, patient outcomes should be more positive based upon an increased stimulus of activity as well as providing moderate stretch for a prolonged period with the new devices. The cycling or repeated extension and contraction of the joint by the new devices provides the additional benefits of motion (activity), increased lubrication of the tissues (production of synovial fluid) facilitating movement, and muscle re-education and diminished spasticity where neurological dysfunction is present (stroke, closed head injury, MS, etc.). The level of activity is higher with the new devices when high tone, spasticity, or moderate to high contraction reflexes are present in the affected limb and joint. Thus the new devices are uniquely appropriate for contractures due to immobility where neurological dysfunction is present in the affected limb.

SUMMARY OF THE INVENTION:

In accordance with the present invention, there are provided orthotic devices, for example, in combination with electrotherapy, useful for extending the range of angular movement between adjacent first and second skeletal body parts which have been drawn to and involuntarily held in a shortened or restricted angular position (limited to a narrow range of motion) relative to one another by contraction of muscles and connective tissue due to immobility. Each such orthotic device comprises a first orthotic device portion, a second orthotic device portion, and means interconnecting the first and second orthotic device portions for permitting relative angular motion therebetween. Included are means for establishing an initial angle between the first and second orthotic device portions.

Further comprising the orthotic device are means for operatively applying or connecting the first orthotic device portion to the first body part and the second orthotic device portion to the second body part after the first body part has been pivoted, by an externally-applied force, to an increased angular position relative to the first body part, the first and second orthotic device portions being then set by the establishing means at the initial angular position relative to one another which corresponds to the increased angular position of the second body part relative to the first body part.

Spring means are connected between the first and first orthotic device portions for urging the second orthotic device portion to return to its initial angular position relative to the first orthotic device portion when the second orthotic device portion is pulled by the applied first body part through muscular contraction and/or the elastic properties of the muscles and connective tissue from the increased angular position toward the second angular position of the first body part relative to the first body part, thereby pulling the second body part back toward the increased angular position relative to the first body part.

The spring means are configured so that pivotal movement of the second orthotic device portion relative to the first orthotic device portion away from the increased angular position causes a restoring loading of the spring means. This restoring loading of the spring means and the muscular contraction and/or the elastic properties of the muscles and connective tissue of the first body part act against one another and cause the second body part to cycle angularly toward and away from the first angular position and the increased angular position without further external intervention, thereby causing a gradual angular loosening of the second body part relative to the first body part and ultimately positioning the second body part at the increased angular position without the application of other forces.

The spring means are further configured for providing substantially no or a low load spring force between the first and second orthotic device portions when the second orthotic device portion is at the initial angular position relative to the first orthotic device portion.

In one embodiment of the invention, the first body part comprises the individual's upper limb part and wherein the second body part comprises the individual's lower limb part, the limb being the individual's arm or leg.

In such case, the first orthotic device portion includes a first cuff and the second orthotic device portion includes a second cuff. The applying means releasably attaches the first cuff to the lower limb part and releasably attaches the second cuff to the individual's upper limb part.

The interconnecting means comprise at least one stiff member having a first end region fixed to the first cuff and a second end region fixed to the second cuff and including a hinge intermediate the first and second end regions for enabling relative angular movement therebetween in a plane defined by the longitudinal axis of the limb upper and lower parts.

Means are included for releasably locking the hinge at any selected angular position of the first end region relative to the second end region. The hinge may also or alternatively include a ratchet for enabling the opening of the first end region relative to the second end region from one angle therebetween to a larger angle therebetween.

Preferably, the spring means comprise relative outwardly bowing and twisting of the first and second end regions of the member when the second end region of the bar is pivoted from the initial angular position relative to the first end region to a smaller angle therebetween.

In a variation orthotic device, the orthotic device of the present invention comprises a thermal setting, flexible member having first and second regions defined by a bend line between the first and second member regions, a bend at the bend line being set by heating, bending and cooling the member at the bend line, the bend line permitting angular movement and enabling the setting of a selected angle between the first and second member regions.

Means are included applying or attaching the first member region to the first body part and the second orthotic device portion to the second body part after the second body part has been moved against contracture forces away from the LROM position to an initial extended range of motion (ROM) angular position relative to the first body part, the first and second member regions being then set at the initial extended range of motion position relative to one another.

Also includes are spring means associated with the first and second member regions for urging the second member region to return to the extended ROM position in response to the second member region being pulled by the applied or attached first body part through muscle fiber contraction and/or the elastic properties of the muscle fibers and connective tissue away from the extended ROM position and toward said LROM position, thereby causing a cycling movement of the second body part between said extended ROM and LROM angular positions and a gradual loosening of the second body part relative to the first body part and an ultimate extending of the ROM of the second body part relative to the first body part at the extended ROM position without additional external intervention.

The spring means are configured for providing substantially no or a low load spring force between the first and second orthotic device portions when the second orthotic device portion is at the initial extended ROM angular position relative to the first member region.

In one version, the first body part comprises the individual's forearm at the wrist and the second body part comprises said individual's hand. In another version, the first body part comprises the individual's lower leg at the ankle and the second body part comprises said individual's foot.

In another version, the first body part comprises the individual's back at the neck and the second body part comprises the individual's head. In another version, the first body part comprises an upper region the individual's back and the second body part comprises a lower region of the individual's back.

In still another version, the first body part comprises an individual's upper thigh after lower regions of the leg have been amputated and the second body part comprises a lower region of the individual's torso at the hip.

In yet another version, the body part comprises the individual's forearm at the wrist and the second body part comprises said individual's hand.

In the orthotic device for each of the pairs of body parts it is preferred that the spring means are provided by flexibility of the elastic member.

In a particularly useful embodiment, the present invention is directed systems comprising orthotic devices, for example, such as those described herein, and electrode components positioned to be effective to conduct an electrical current to at least one body part of a patient being treated. The orthotic device preferably is adapted to extend the range of angular movement between adjacent first and second skeletal body parts which have been drawn to and involuntarily held in a limited angular range of motion position relative to one another by contraction of muscle fibers and connective tissue due to immobility of one or both of said skeletal body parts. The electrode components preferably include a plurality of individual electrically conductive elements or electrodes strategically placed relative to the orthotic device, for example, in or on the orthotic device, to combine orthotic treatment and electrotherapy. A power source, for example, an electrotherapy unit, such as those of conventional design, disposable units and the like, is used to provide electrical power or energy to the electrode component so that electrical current can be provided to the desired body part or parts. Although the orthotic device may be worn by the patient for several hours, the electrotherapy may be actually used for either all or a portion of the time the orthotic is worn.

The combination of electrotherapy and an orthotic device has many advantages over the separate use of each modality. The electrotherapy can be activated through the strategic placement of a plurality of conductive elements or electrodes, for example, in or on the orthotic device to provide numerous therapeutic benefits. Electrotherapy can elicit partial to total muscle inhibition to allow the orthotic device to provide superior muscle stretch and to eliminate the pain and discomfort sometimes experienced by the wearing of an orthotic device. Muscle strengthening and re-education, muscle contraction inhibition, increased blood flow, nerve stimulation and neuro-pathway reconstruction, and other benefits can also be provided while the patient wears the orthotic device. By combining the application and therapeutic benefits of both modalities in one device, therapeutic patient outcomes as well as patient compliance are often significantly increased. The electrotherapy/orthotic therapy combination preferably reduces the treatment time required relative to the treatment time required if each therapy is provided separately.

Many advantages are evident in the combination of the two modalities. A few of the benefits include:

(1) inhibiting contraction of the contracted muscles, tendons, and connective tissue to allow the orthotic device to provide "long effects" or permanent stretch therapy for a greater period relative to using only one of the modalities;

(2) muscle strengthening and re-education of the "antagonist" muscles to provide longer lasting permanent stretch and joint range of motion. By strengthening the antagonist muscle group opposing the "shortened" or contracted muscle group, the "effect" of the contracted muscles is diminished and the muscles are maintained in a stretched permanent position;

(3) by enhancing the development of new neuro-pathways to the brain so that muscle groups non-responsive to brain function can be significantly improved, providing greater post stroke or other neurological disorder rehabilitation, resulting in an improved use of the effected side;

(4) increasing blood flow, reducing swelling, and enhancing the production of synovial fluid will enhance joint movement.

(5) providing muscle contraction inhibition and/or nerve block electrotherapy with the ability of the orthotic device to provide Low Load Prolonged Stretch (LLPS) conveniently allows maintaining an optimal setting of the orthotic device. The orthotic device setting is effectively self adjusted, for example, by a ratchet-like hinge, to the gains made via the electrotherapy portion of combined therapy device. Thus, numerous device checks or modifications become unnecessary; and (6) The combination of electrotherapy with orthotic stretch requires significantly less therapy or caregiver intervention to enhance therapy.

There are other potential benefits to having an electrotherapy component built into the orthotic device. The list of benefits cited is not meant to be exhaustive, only to provide insight as to the benefit of the present invention to the field of contracture management. The soft goods and/or hard goods of the present orthotic device can be configured appropriately to provide the desired therapeutic result.

BRIEF DESCRIPTION OF THE DRAWINGS

The present invention may be more readily understood when taken in conjunction with the accompanying drawings in which:

FIG. 1 is a pictorial diagram depicting, in diagrammatic form, the condition of typical muscle and connective tissue across a joint.

FIG. 2 is a pictorial drawing of an upper region of an individual, showing in solid lines, by way of illustrative example, the individual's arm involuntarily held in a bent position with the forearm at a high LROM angle, $\alpha_0$, with respect to the upper arm, and further showing, in phantom lines, the forearm extended at increasing angles $\alpha_1$ through $\alpha_4$ relative to the upper arm by application of the present orthotics invention;

FIG. 4 is a partially exploded, perspective drawing of a representative elbow orthotic device of the present invention which is constructed for providing gradual extension of a human arm about an elbow joint from an initial, involuntary tight angle $\alpha_0$ to an extended angle $\alpha_4$ which enables the individual to restore full or partial ROM of his or her arm;

FIG. 12 is a perspective drawing of a leg- or knee-type orthotic device according to the present invention, showing features of the device and showing the device operatively installed on an individual's knee;

FIG. 13 is a perspective drawing of a hip abductor-type orthotic device in accordance with the present invention showing useful in treating hip contracture which limits the range of motion of one leg of an individual relative to the other leg of the individual, that is, when the leg is maintained by contracture crossed over the other leg;

FIG. 19 is a perspective drawing of an upper torso-type orthotic device in accordance with the present invention for treating contracture of an individual's upper body in which the upper body is bent forward or to one side and showing construction of the device and showing means for detachable attaching the device to an individual's upper body;

FIG. 20 is a perspective drawing of an ankle-type orthotic device in accordance with the present invention for treating contracture of an individuals foot relative to his or her ankle in which the toe portion of the foot is held by contracture substantially straight down with respect to the ankle and showing construction of a boot shaped assemble and means for holding a sole of the boot against the toe portion of the foot;

In the various FIGS. identical elements and features are given the same reference number, and similar or corresponding elements and features are or may be given the same reference numbers followed by an a, b, c, and so on, as appropriate and as will be evident, for purposes of describing the various orthotic devices of the present orthotic device invention.

DESCRIPTION OF THE PREFERRED EMBODIMENT

Figure 3:
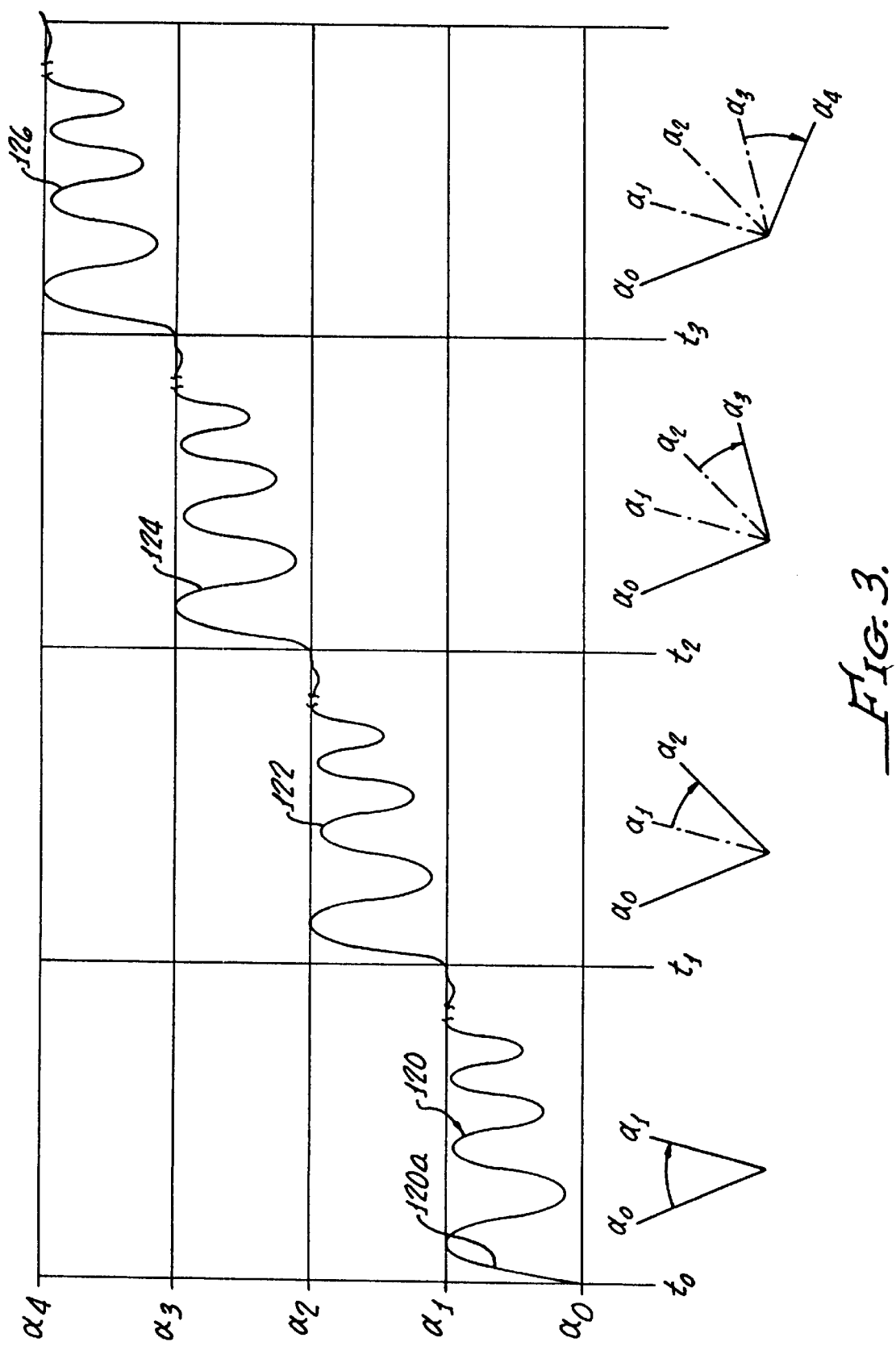
FIG. 3 is a illustrative graph in which forearm angles $\alpha_0$ through $\alpha_4$ of FIG. 2 are plotted against representative intervals of treatment time, depicting several exercise cycles of the individual's arm by use of the present orthotic invention to increase the bend or ROM angle between the forearm and the upper arm from $\alpha_0$ to $\alpha_1$ in time interval $t_0$ to $t_1$, from $\alpha_1$ to $\alpha_2$ in time interval $t_1$ to $t_2$, from $\alpha_2$ to $\alpha_3$ in time interval $t_2$ to $t_3$, and from $\alpha_3$ to $\alpha_4$ in time interval $t_3$ to $t_4$.

The present inventor suggests that a better understanding of the present orthotic device invention may be had by a more detailed consideration of FIGS. 1–3 which depict the operative aspects of the present invention. It is thus believed that a brief consideration of how and why the orthotic devices of the present invention work will lead to an understanding of the orthotic devices which are described below.

As briefly mentioned above, FIG. 1 depicts—by way of an illustrative example for descriptive purposes, with no limitation being thereby intended or implied—a simplified diagram of a representative bundle or matrix of muscle fibers and connective tissue which may control ROM of typical joint, for example, an elbow of a human being.

Figure 1A:
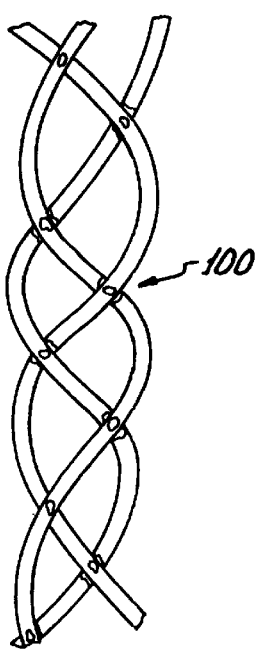
FIG. 1A depicting the normal condition of a typical bundle or matrix of normal muscle and connective tissue fibers.
Figure 1C:
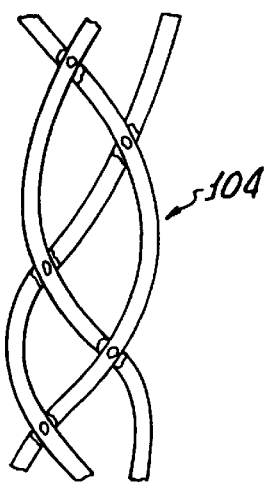
FIG. 1C depicting the same bundle of muscle and connective tissue fibers similar to normal muscle and connective tissue, but having become shortened as a result of immobility.
Figure 1B:
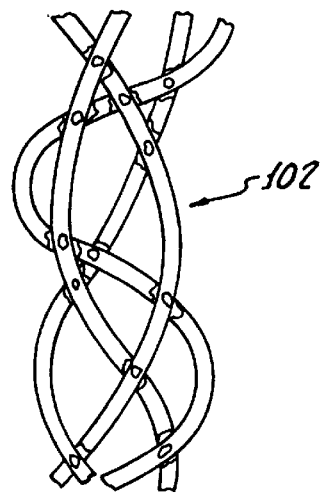
FIG. 1B depicting the same bundle of matrix of muscle and associated connective tissue in a tangled condition associated with post-trauma conditions and showing adhesion of the muscle and connective tissue fibers.

FIG. 1A depicts a representative bundle or matrix 100 of muscle and connective tissue in a normal state or condition. FIG. 1B depicts a similar, representative bundle 102 of muscle fibers and connective tissue in a twisted and distorted, post-trauma state or condition. In turn, FIG. 1C depicts a similar, representative bundle 104 of muscle fibers and connective tissue in a shortened, but non-distorted state or condition as a result of immobility.

The present invention, as described below, is designed and constructed to provide treatment for muscles and connective tissue on various parts of the human body skeletal system which are in the condition of bundle of muscle fibers and connective tissue depicted in FIG. 1C as a result of immobility.

An individual's arm and elbow will be hereinafter be considered for the express purposes of describing the present orthotic device invention. It is, however, to be understood that what is described for the arm, and particularly for the elbow, applies in principle to such other skeletal parts of the body as the leg, hip, ankle, wrist, hand, neck and back, which may also suffer limited ROM as a result of immobility, and to orthotic devices therefor in accordance with the present invention.

There is depicted in FIG. 2, for such illustrative purposes, and with no limitation intended or implied, an individual 110 (only the upper torso of which is shown), is depicted having a right arm or limb 112 which comprises an upper arm or upper limb portion 114 and a forearm or lower limb portion 116. Forearm 116 is shown in solid lines in an involuntary, slightly extended ROM angular position, $\alpha_0$, relative to upper arm 114, by contracted muscle and/or interconnecting tissue of the configuration depicted in FIG. 1C and caused by immobility for a protracted period of time due to one or more of the above-mentioned causes. Consequently, the afflicted individual 110 is unable by himself or herself to extend forearm 116 from this $\alpha_0$ position without significant resistance and potential further injury to the afflicted joint (i.e., elbow).

Depicted in phantom lines in FIG. 2, is a sequence of increasingly greater angular ROM positions of forearm 116 relative to upper arm 114, these positions being identified for descriptive purposes by ROM angles $\alpha_1$, $\alpha_2$, $\alpha_3$ and $\alpha_4$. As will become evident from the following description, these increasing ROM angles $\alpha_1$, $\alpha_2$, $\alpha_3$ and $\alpha_4$ represent increasingly greater angular ROMs of forearm 116 relative to upper arm 114 which result from the application to arm 112 of an elbow-type orthotic device in accordance with the present invention.

FIG. 3 depicts in a simplified representation the manner in which the increasing angular ROM of arm 112 as depicted in FIG. 2 may be achieved by use of the present orthotic device invention. As such, FIG. 3 plots angular ROMs of forearm 116 $\alpha_0$, $\alpha_1$, $\alpha_2$, $\alpha_3$ and $\alpha_4$ against representative periods of time, in which initial time $t_0$ corresponds to ROM angle $\alpha_0$, time $t_1$ corresponds to increased ROM angle $\alpha_1$, time $t_2$ corresponds to further increased ROM angle $\alpha_2$, time $t_3$ corresponds to still further increases angle $\alpha_3$, and time $t_4$ corresponds to full extension ROM angle $\alpha_4$.

It is to be clearly understood that although the sequential time periods or intervals to $t_0$ to $t_1$, $t_1$ to $t_2$, $t_2$ to $t_3$ and $t_3$ to $t_4$ are depicted in FIG. 3 for illustrative purposes only, as being equal, in practice, the actual time intervals will usually be different, and, in fact, may be significantly or greatly different.

The objective of FIG. 3 is to depict the general situation in which the increased ROM of the individual's forearm 116 relative to upper arm 114 from $\alpha_0$ to $\alpha_1$, over some time interval $t_0$ to $t_1$, is gradually achieved through a series of forearm arm extension and contraction cycles, identified by the reference number 120. Initial extension of forearm 116 to ROM angular position $\alpha_1$ depicted by initial portion 120a of cycles 120, is caused by manual massage and slow extension of the forearm 116 to the point of resistance to passive stetch.

When angular position $\alpha_1$ of forearm 116 is reached through such manual manipulation, the elbow orthotic device (described below) of the present invention is applied to arm 112 and the forearm is released. Thereafter the angular cycling of forearm 116 relative to upper arm 114 is caused by the counter action of contracture of the individual's muscle and/or connecting tissue across the elbow, which tend to pull the forearm back toward its initial shortened involuntary ROM angle $\alpha_0$ relative to the upper arm, and the restoring spring force of the present orthotic device, which operates to pull or extend the forearm back to the extended ROM angle $\alpha_1$ relative to upper arm 114.

At time $t_1$, depicted in FIG. 3, and after a number of retraction and extension cycles as described above, the angular ROM of forearm 116 relative to upper arm 114 has been increased to ROM angle $\alpha_1$ such that individual 110 will be able to move his or her arm 112 to this extended ROM angular position without mechanical or other assistance. It is, however, to be appreciated that some reinforcement treatment may from time to time be required to maintain this increased angular ROM.

It is again emphasized that the extension-retraction cycles in sequence 120, although shown regular in nature for illustrative and descriptive purposes, will, in practice, likely vary in number, length of time and magnitude, depending upon such factors as condition of the associated muscular and connective tissue (hypertonicity, spasticity, contraction reflexes, etc.) length of the immobility time, and age and general health of the patient.

At time $t_1$, when the angular ROM of the individual's forearm 116 has been increased to $\alpha_1$, the orthotic device is loosened or removed from arm 112 and the forearm is manually massaged and slowly stretched to an increased ROM angle $\alpha_2$. The orthotic device of the present invention is retightened or reapplied to arm and is reset to angle $\alpha_2$. Forearm 116 is released and cycles through a sequence 122 of angular contraction and extension movement in the manner just described for increasing the angular ROM of the forearm to $\alpha_1$ until the angular ROM of forearm 116 is increased to angle $\alpha_2$.

This procedure is repeated through a sequence of contraction and extension cycles 124 to increase the angular ROM of forearm 116 relative to upper arm 114 from $\alpha_2$ to angle $\alpha_3$, and finally through a sequence 126 of contraction and extension cycles of forearm movement until a full ROM of the forearm, depicted by angle $\alpha_4$ has been achieved.

It is, of course, to be understand that more or less that the four angular extension steps depicted in FIG. 3 may be required in actual practice and may vary considerably from individual to individual. In addition, the sequence of steps achieving ROM increase from its initial LROM angle $\alpha_0$ to the full range of motion associated with $\alpha_4$ may require hours, days, weeks or even months, according to the length of time forearm 116 has been contracted and the condition (hypertonicity, tone, spasicity, contraction reflexes, etc,) of the muscles and connective tissue and fibers associated with movement of the forearm.

Elbow- or Arm-Type Orthotic Device of FIGS. 4–11:

By way of continuing the illustrative example started above, FIG. 4 shows in exploded form a elbow- or arm-type orthotic device 140 in accordance with the present invention. Elbow-type orthotic device 140 will be described in detail as an introduction to other types of similarly functioning orthotic devices included in the present invention and which will be described hereinbelow.

Elbow-type orthotic device 140 is specifically configured for treating contracture of arm 112 relative to elbow 142 and thereby to achieve the extended angular ROM depicted in FIGS. 2 and 3.

As shown in FIG. 4, elbow-type orthotic device 140 comprises generally a stiff U-shaped first orthotic device upper arm portion or member 144 and a similar, stiff U-shaped second orthotic device lower arm portion or member 146. First and second device portions 144 and 146 are connected together in a manner enabling relative angular motion therebetween and are, in fact, hinged together by connecting means 148, as more particularly described below.

Further included in elbow-type orthotic device 140 are a first, upper arm padded cuff 150 and a similar, second, lower arm padded cuff 152. Means for detachably attaching device 140 to arm 112 comprise an adjustable upper strap 154 that is attached to device upper member 144 and an adjustable lower strap 156 that is attached to device lower member 146.

The means 148 for interconnecting upper and lower portions 144 and 146 comprise elongate first, right side and second, left side mirror-image connecting assemblies 160 and 162, respectively. As shown in FIGS. 4, 6, 8 and 10, right side connecting assembly 160 comprises similar upper and lower elements 166 and 168, respectively.

Adjacent ends of elements 166 and 168 are connected for relative angular movement therebetween by a lockable hinge 170. In the same manner, left side connecting assembly 162 comprises corresponding upper and lower elements 174 and 176, respectively, adjacent ends of which are connected for relative angular movement therebetween by a lockable hinge 178.

Figure 10:
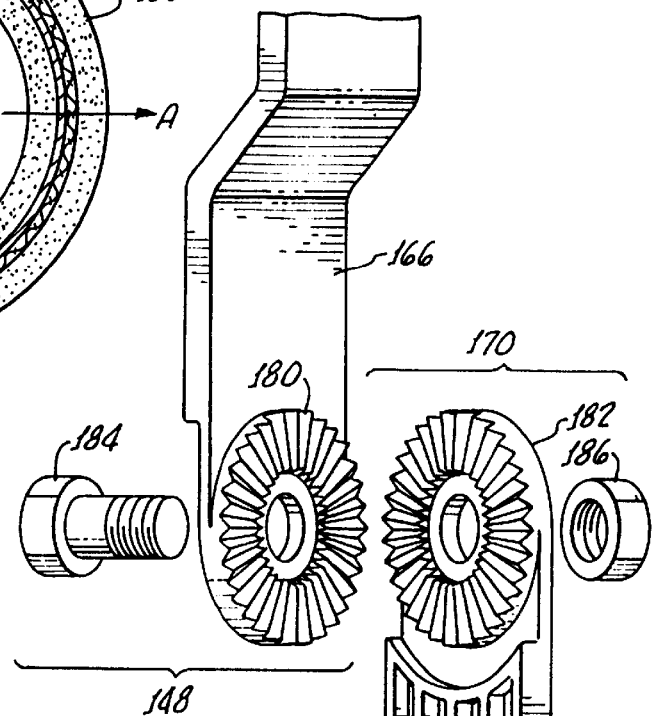
FIG. 10 is perspective drawing of a representative one of the hinged interconnecting members, showing the first and second end portions disassembled at the hinge and showing the manner in which the hinge holds the two end portions in a fixed relative position.

As shown in disassembled condition in FIG. 10, right-hand lockable hinge 170 includes mating first and second toothed end regions 180 and 182 of respective elements 166 and 168. When assembled and tightened together a bolt 184 and nut 186, end regions 180 and 182 intermesh to lock upper and lower elements 166 and 168 in any selected relative angular position. A left lockable hinge 178, is constructed in the same way, not specifically shown.

Figure 11:
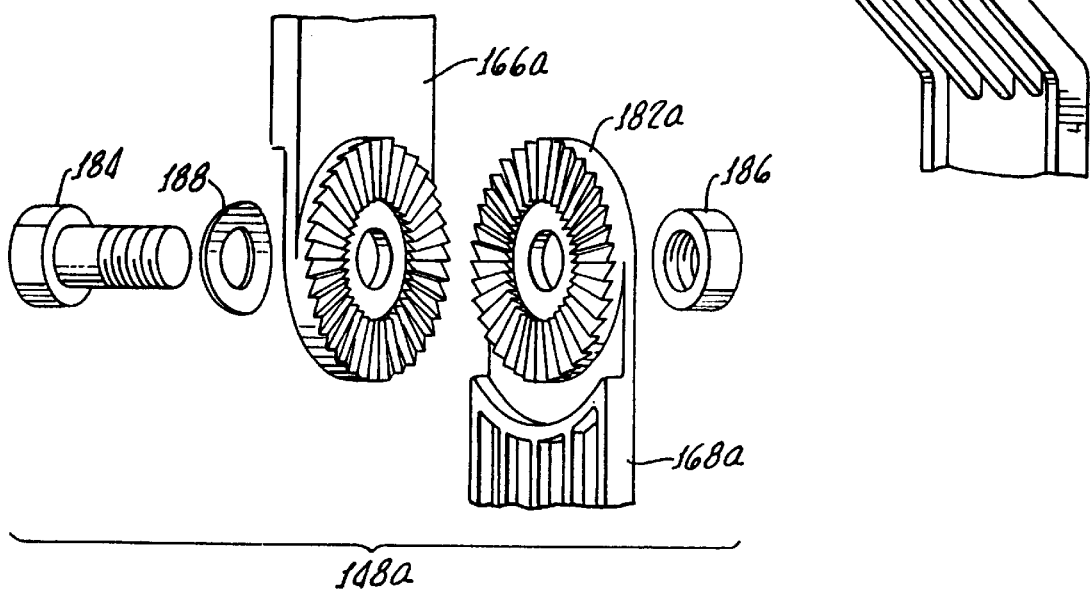
FIG. 11 is a perspective drawing of an alternative lockable hinge connection between first and second device portions of a hinged interconnecting member, showing a ratchet configuration of the hinge connection which permits easier and more rapid extension between the two portions.

In the alternative connection configuration depicted in FIG. 11, a corresponding right-hand hinge 170a between respective upper and lower elements 166a and 168a has first and second mating regions 180a and 182a having teeth shaped for enabling a ramping or ratcheting action for easy opening of the upper and lower elements to greater angles therebetween, while inhibiting the closing of the elements. Upper and lower elements 166a and 168a are fastened together by a bolt 184 and nut 168. A spring-type washer, for example, a Belleville washer, 188 is installed on bolt 184 so that lower element 168 can be ratcheted to a greater angle position relative to upper element 166 without completely withdrawing bolt 184 from nut 186.

Figure 7:
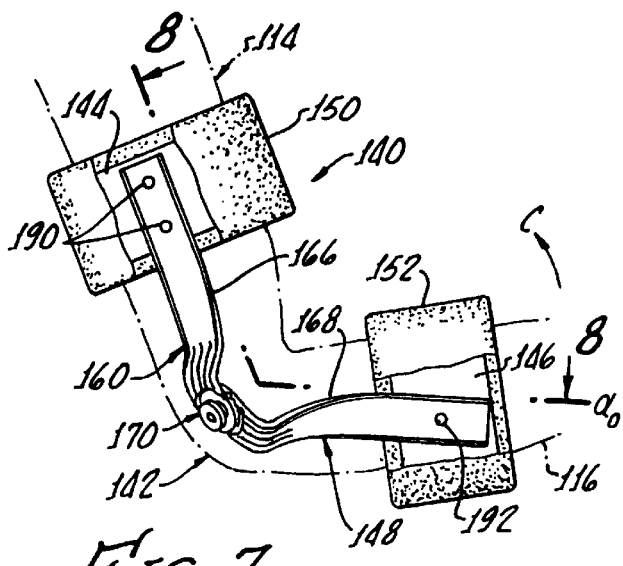
FIG. 7 is a side view of the elbow orthotic device of FIG. 4 showing the device operationally installed onto the individual's arm with the upper and lower arm returned to initial ROM angle $\alpha_0$ (referring to FIGS. 2 and 3) showing flexure of the hinged interconnecting elements.
Figure 8:
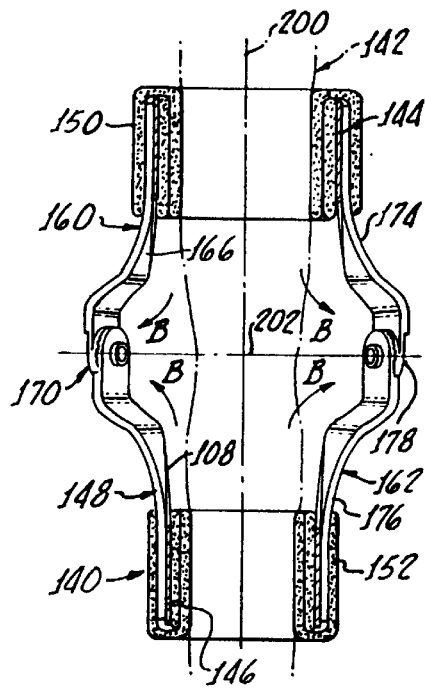
FIG. 8 is a longitudinal cross sectional view taken along line 8—8 of FIG. 5, showing the pair of hinged interconnecting elements flexed and twisted outwardly at the hinge point in a manner providing a torsion spring force to urge the return of the orthotic device and the wearer's arm to the initial open position of angle $\alpha_1$.

As depicted in FIG. 7 for right side connection assembly 160 (typical also for left side connection assembly 162) the upper end region of upper element 166 is non-pivotally attached to a right-hand side region of device upper member 144, for example, by two rivets, screws or the like 190. A lower end region of lower element 168 is pivotally attached to a right-hand side region of device lower member 146 by a single pivot pin or screw 192.

Upper and lower left hand elements 174 and 176 of connection assembly 162 are attached to generally opposite sides of respective upper and lower device members 144 and 146 in the manner described for connection assembly 160.

Figure 9:
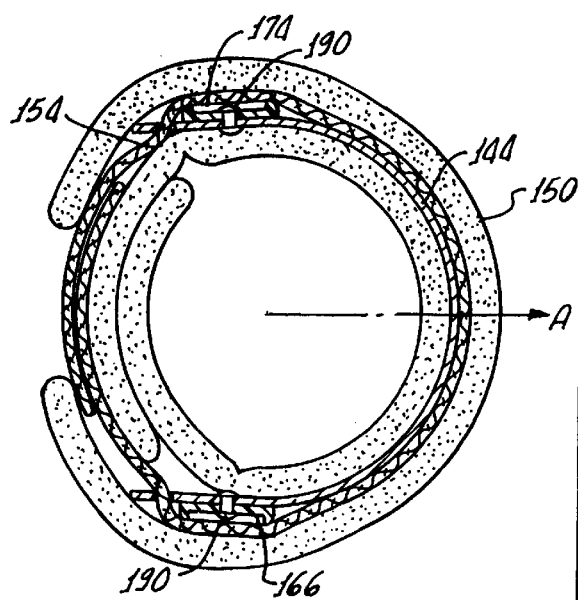
FIG. 9 is a transverse cross sectional drawing taken along line 9—9 of FIG. 5, showing the manner in which an upper end region of the orthotic device is releasably attached to the individual's upper arm.

As shown in FIG. 9, upper elements 166 and 174 are attached to opposite side regions of upper portion 144 in off-center positions. Assuming arrow A points to a 12 o'clock position of upper member 144, elements 166 and 174 are attached to the upper member at about 4 o'clock and about 8 o'clock positions, respectively. The attachment of lower elements 168 and 176 are attached to lower member 146 in a similarly offset manner. Such offset attachments enable appropriate spring action of connecting assemblies 160 and 162, as described below.

Figure 6:
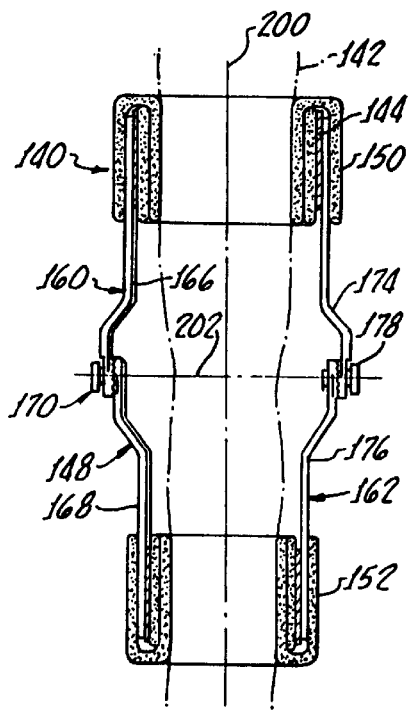
FIG. 6 is a longitudinal cross sectional view taken along line 6—6 of FIG. 5, showing upper and lower arm cuffs of the elbow orthotic device, and showing construction of an associated pair of interconnecting hinged elements which also function as orthotic device return springs.

Upper and lower elements 166 and 168 of right connecting assembly 160 are constructed, as shown in FIG. 6, which represents orthotic device 140 in the unloaded or initially set angular position $\alpha_1$ of device 140, as being slightly bowed outwardly in the region of hinge 170 from a central longitudinal axis 200. In a similar manner, elements 174 and 176 of left connecting assembly 162 are constructed for being slightly bowed outwardly from axis 200 in the region of hinge 178.

Right and left connecting assemblies 160 and 162 are thus bowed outwardly from longitudinal axis 200 in opposite directions along a transverse axis 202. This configuration, as well as the offset mounting described above causes hinge regions of connecting assemblies 160 and 162 to be twisted outwardly in the direction of Arrows "B" (FIG. 8) to create a restoring force whenever hinges 170 and 178 are locked and device 140 is contracted in an angular direction of Arrow "C", FIG. 7.

In operation, referring to FIG. 2, forearm 116 of arm 112 is gradually moved by a manual massaging action from its LROM angular position depicted at angle $\alpha_0$ to initial extended ROM angle $\alpha_1$ which is selected to be as far as forearm 116 can be extended without inflicting damage to muscles and connective tissue between the forearm and upper arm 114.

Referring to FIGS. 4–6 and 9, with forearm 116 held in this extended position of $\alpha_1$, bolts 184 of hinges 170 and 178 of orthotic device 140 are loosened so that upper device member 144 can be fit onto upper arm 116 and attached thereto by first strap 154, cuff 150 being used to pad the upper portion and protect the upper arm. In a like manner, lower member 148 is fit onto and attached to forearm 116 by second strap 156. Hinges 170 and 178 are then locked into position by tightening bolts 184 so that device 140 conforms to the ROM angle (i.e., ROM angle $\alpha_1$) between individual's forearm 114 and upper arm 116. At this point, connecting assemblies 160 and 162 are unstressed and provide no force whatsoever on arm 112 as long as the arm is held at ROM angle $\alpha_1$.

Figure 5:
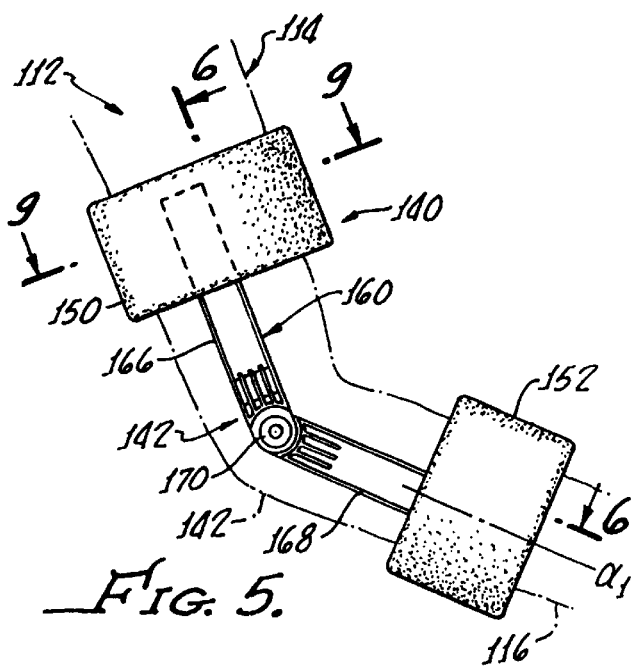
FIG. 5 is a side view of the representative elbow orthotic device of FIG. 4, showing the device operationally installed onto the individual's arm in a manner bridging the individual's elbow, with the upper and lower arm held at an initial stretched ROM angle $\alpha_1$ (referring to FIGS. 2 and 3)

With orthotic device 140 attached to arm 112 as described above at arm ROM angle $\alpha_1$ and with the arm held (by other than the orthotic device) and as depicted in FIGS. 5 and 6, the arm is then released and forearm 116 is pulled back (in the direction of Arrow "C", FIG. 7) toward LROM angle $\alpha_0$ by the previously stretched muscles and connective tissue across elbow 142.

Connecting assemblies 160 and 162 thus function as torsion springs which, as they are increasingly twisted outwardly by contracture of arm 112, store increasing amounts of energy as forearm 116 increasingly contracts back toward upper arm 114. At some angular return position between $\alpha_1$ and $\alpha_0$, the restoring spring energy in connection assemblies 160 and 162 and the contracture force attempting to return forearm to its LROM angle $\alpha_0$ equalize and the return contractive movement of forearm 116 ceases. Thereafter, the muscle fibers and connective tissue across elbow 142 start relaxing or weakening, and the stored torsional energy in connecting assemblies take over and start to pull forearm back toward ROM angle $\alpha_1$. At some time before or as forearm 116 reaches back to angle $\alpha_1$, the contractile forces on arm 112 take and once again start pulling the forearm back towards LROM angle $\alpha_0$ relative to upper arm 114. The cycling of forearm 116 back and forth between LROM angle $\alpha_0$ and extended angle $\alpha_1$, is repeated, as indicated in the time interval $t_0$ to $t_1$ depicted in FIG. 3, until the muscle fibers and connective tissue across elbow 142 are stretched to the point that they no longer provide any contracting force at ROM angle $\alpha_1$.

With device 140 remaining attached to arm 112, device hinges 170 and 172 are then loosened and forearm 116 is massaged against contracture forces until the forearm is stretched as far as possible without injury to muscle fibers and connective tissue to a new ROM angle $\alpha_2$. Hinges 170 and 172 are retightened and forearm 116 is then released. Alternatively, when ROM angle $\alpha_1$ has been attained, device 140 may be removed from arm 112 and may be reinstalled after hinges 170 and 172 have been reset to ROM angle $\alpha_2$.

The cycling of forearm 116 between ROM angle $\alpha_2$ and ROM $\alpha_1$ then starts upon release of forearm 116 and continues in the above-described manner until the arm can stay at ROM $\alpha_2$ on its own.

The above-described process is repeated through ROM angle $\alpha_3$ until a full ROM angle of arm 112 is attained, for example, ROM angle $\alpha_4$ at time $t_4$ as depicted in FIG. 3.

The alternative use of ratcheting type of hinges 170a and 172a depicted in FIG. 11 make the above-described steps of increasing the angle of connecting assemblies 160a and 162a easier. The ratcheting action of hinges 170a and 172a depicted in FIG. 11 also allow progression from $\alpha_1$ to $\alpha_2$ to occur without the need to manually adjust the hinge setting as the limb "relaxes" or "fatigues" allowing additional extension during the "relaxed" phase of contraction and extension cycling.

Device connecting assemblies 160 and 162, as well as 160a and 162a, are preferably constructed of a stiff elastomeric plastic material, such as polyurethane or fiberglass. As with entire device 140, dimensions of connecting assemblies 160 and 162 are necessarily varied in dimensions, as can be determined by one skilled in the relevant art, according to the age, size and muscular and interconnecting tissue characteristics of the individual to be fitted with the device and further according to the extent of LROM of the individuals arm and the duration and type of immobility which has caused contracture of arm 112.

It will be appreciated that the same principle of operation described above for device 140 is used with the below-described other types of orthotic devices which are within the scope of the present invention. By other types it is meant types of orthotic devices that are specifically designed for other skeletal parts of the body such as knee, wrist, ankle and so forth. The main differences in the various types of orthotic devices disclosed herein are the means for attaching the devices to the body or for causing one or both of the main parts of the device to bear operatively against an associated part of the body. Consequently, description of the devices will be concentrated on the principal differences between the device being described and device 140 which is described above in detail.

Knee- or Leg-Type Orthotic Device of FIG. 12:

FIG. 12 depicts a knee- or leg-type orthotic device 200 in accordance with another embodiment of the present invention. Because of the similarity between elbow 142 and a knee 202 it will be readily understood that knee-type device 200 is virtually identical with above-described elbow-type device 140 except for a shaped knee retainer 204 that is detachably attached to connection assemblies 160a and 166a (which correspond directly to connection assemblies 160 and 166 of device 140) so as to keep knee 202 from slipping through the device.

Connection assemblies 160b and 166b are attached to respective upper device member or portion 144a and lower member or portion 146a in the same offset manner described above for corresponding upper and lower members 144 and 146 of device 140. Upper and lower members 154a and 156a respectively are detachably installed on leg 210 in the same way upper and lower members 154 and 156 are attached to arm 212, that is, the upper and lower members are attached to respective upper leg or thigh 212 and lower leg 214 by respective straps 154a and 156a, and are covered with padded cuffs 150a and 152a to protect leg 210.

In FIG. 12, leg 210 is shown in solid lines at ROM angle $\alpha_1$ and in phantom lines at LROM angle $\alpha_0$.

The operation of knee-type orthotic device 200 is identical to the operation of arm-type orthotic device 140 described above and does not, therefore, require any description.

Hip Abduction-Type Orthotic Device of FIG. 13:

In some contracture conditions, including hip abduction, knee abduction and scissoring of the lower limbs, and as depicted in FIG. 13, an ankle region of one leg 220 of an individual is held in the LROM position against (as indicated in phantom lines) or crossed over the ankle region of other leg 222. This condition can understandably prevent the individual from walking or engaging in any activity requiring the use of an individual's legs.

In such a condition, the therapeutic objective is to restore normal ROM of legs 220 and 222 relative to one another by use of a hip abduction-type orthotic device (or knee abduction device) 224 which comprises a connection member 160c (similar to above-described connection member 160) which is connected between ankle regions of respective right and left ankle boots 226 and 228.

In this regard, a distal end of right portion 166c of connection member 160c is attached to an rear, ankle region of right boot 226 by a pivot pin 230 and a distal end of left portion 166c of member 160c is attached to a rear, ankle region of left boot 228 by a pivot pin 232. Proximal ends of member portions 160c and 168c are interconnected by a hinge assembly 170c.

Each connection member portion 166c and 168c is shown in phantom lines in FIG. 13 at a LROM angle $\alpha_1$ relative to a vertical axis or plane 234. Shown in solid lines in FIG. 13, connection member portions 166c and 168c are at post-treatment ROM angles $\alpha_4$ relative to vertical plane or axis 234.

Step-wise operation of hip-type device 224 is exactly as described above for elbow-device 140 and knee-device 200, with connection member 160c functioning as a spring pulling legs 220 and 221 apart in response to contracted muscle fibers and connective tissue at the hip joint pulling the legs together.

Figure 14:
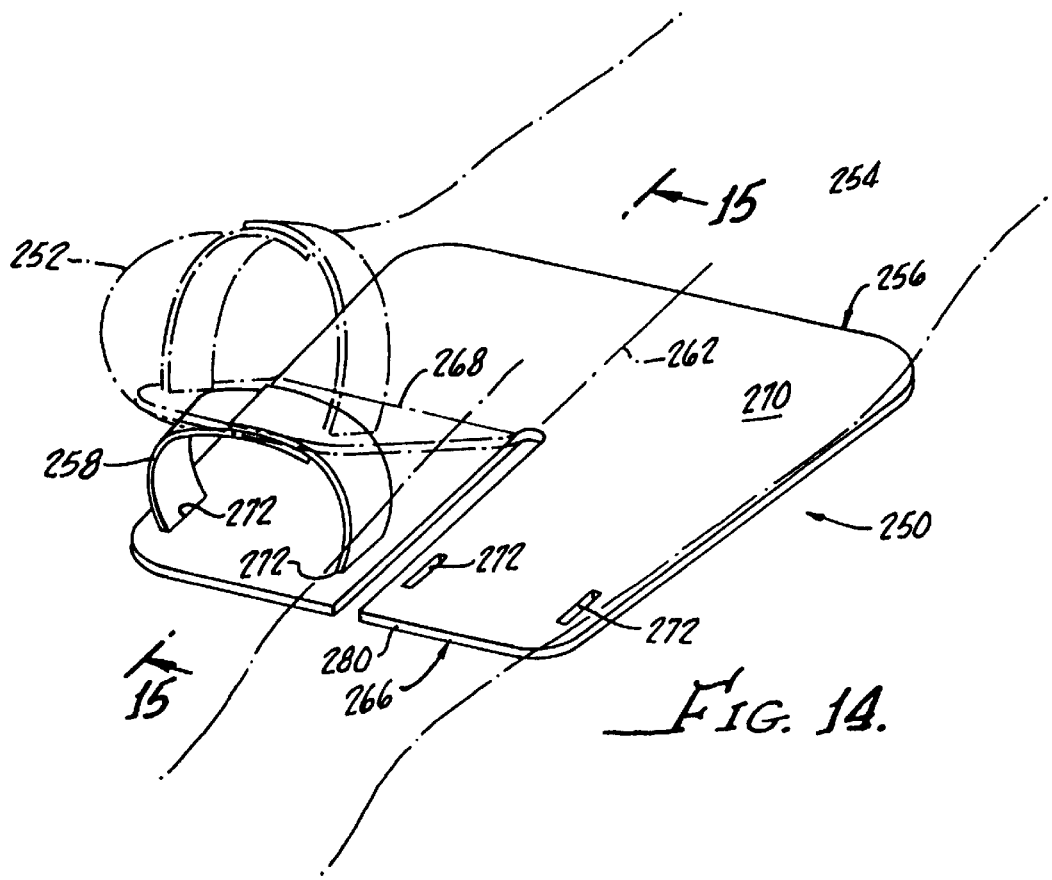
FIG. 14 is a perspective drawing of an orthotic device in accordance with the present invention for the therapeutic treatment of contracture of a representative portion (stump) of an upper leg after the amputation of the remaining, lower portion of the leg, showing a substantially flat thermal-setting, plastic member having a first portion to be weighted down by the individual's buttocks and a second portion for detachable attachment to the stump.
Figure 15:
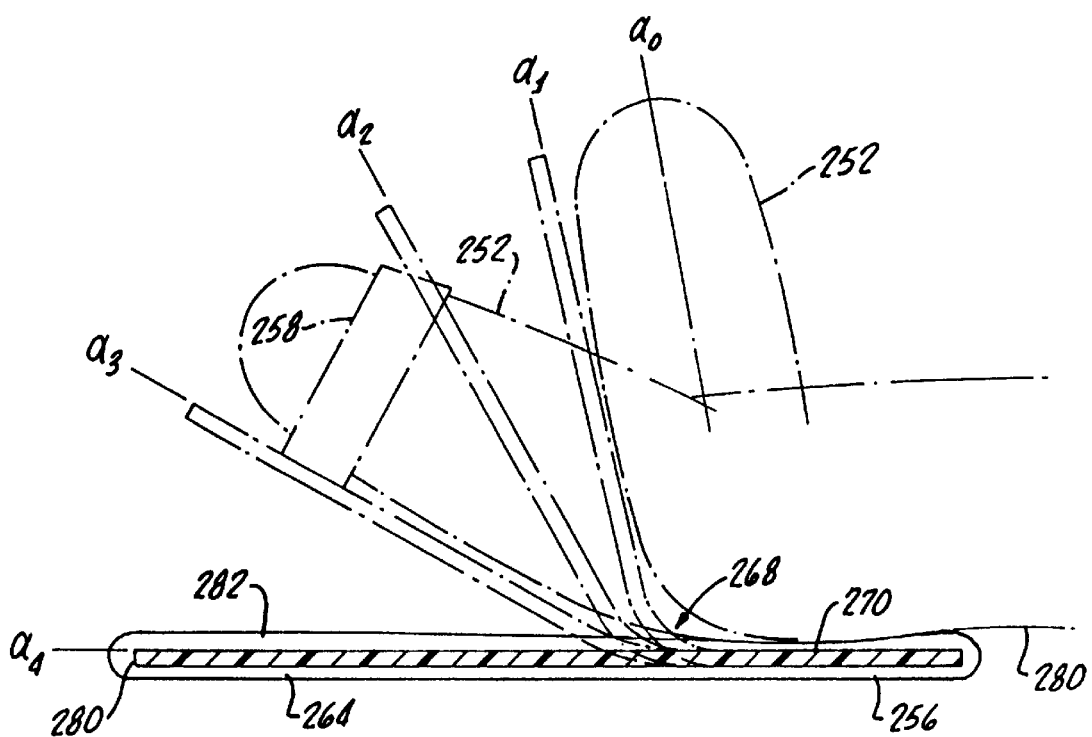
FIG. 15 is a longitudinal cross sectional drawing taken along line 15—15 of FIG. 14 showing the manner in which the second portion of the device is manually bent (by heating of the device) in steps from an initial treatment ROM angle $\alpha_1$ to an extended ROM angle $\alpha_4$.

Amputated Leg-Type Orthotic Device of FIGS. 14 and 15:

A number of regions of the body can be afflicted by contractures but which are not configured in such a manner that the orthotic devices of the present invention cannot be configured in the manner of elbow-type and knee-type orthotic devices 140 and 200 described above. Nevertheless, the principle of the above-described operation to overcome contractures of these other parts of the body is essentially identical to that described for orthotic devices 140, 200 and 224.

FIGS. 14 and 15 depict a hip or pelvic control orthotic device 250 in according to the present invention that is useful for the treatment of contracture of a remaining stump portion 252 of an individual's leg after the remaining lower portion of the leg has been amputated.

In the case being considered herein, contracture of stump 252 has caused the stump to point upwardly or outwardly at some LROM angle. FIG. 15 shows stump 252 pointing upwardly or outwardly at a LROM angle $\alpha_0$ relative to the individual's lower body. Not only is such a contracture of stump 252 unsightly and embarrassing to the individual, but in a practical sense makes many sitting or sleeping positions impossible or uncomfortable, makes dressing of the individual very difficult and prevents the use of an orthopedic or artificial leg impossible.

The intent of amputated leg-type orthotic device 250 is to restore, in the manner described above relative to elbow-type orthotic device 140 and knee-type device 200, the full angular ROM of stump 252 relative to the individual's trunk 254. Such restoration will enable the individual to move stump 252, without external assistance, to and from a normal leg position relative to trunk 254 to thereby enable the individual to lead a more normal life.

As shown in FIG. 14, the orthotic device 250 of the present invention comprises a plate or plate portion 256 and a detachable stump attachment element or adjustable strap 258. Plate portion 256 is formed from a flat sheet of thermal-setting plastic, such as KYDEX® or LEXAN®, and is generally rectangular in shape and about one-eighth of an inch in thickness. Plate or plate portion 256 is formed having a split 260 in the thigh region along a longitudinal axis 262, the split defining side-by-side first and second thigh regions 264 and 266, respectively.

A transverse bend line 268 (which can be considered as a hinge line)is defined between thigh regions 264 and 266 at the distal end of split 260, and essentially divides the thigh regions from a seat portion 270.

Depending on which leg has been amputated, attachment element 258 is installed through slots 272 in either first or second thigh regions 264 or 266 adjacent a proximal edge 280. As depicted in FIG. 14, attachment element is installed through slots 272 in first thigh region 264 for use with stump 252 of the individual's right leg. A padded sleeve 282 (FIG. 15) is preferably installed over plate 256 to provide comfort to the individual being treated.

With the individual lying on a firm surface 280, such as a massage table, stump 252 is massaged by another individual, who may be a physical therapist, from its contracture LROM angular position $\alpha_0$ to an initial extended ROM angular position $\alpha_1$ (FIG. 15), which corresponds to the initial ROM angular position described above for devices 140 and 200.

The individual's extended ROM angle $\alpha_1$ of stump 252 is measured by a goniometer, in a well known manner. Device plate 256 is heated along bend line 268 and first thigh region 264 is bent along the bend line to angle $\alpha_1$ (FIG. 15) and is then allowed to cool to "lock" the bend at such angle.

With the individual's stump 252 held at ROM angle $\alpha_1$, he or she is lifted and device 250 is slid under the individual so that potion 270 is beneath the patient's buttocks and so that stump 252 is resting on first thigh region 264. Attachment element 258 is installed around stump 252 and is tightened to securely hold the stump against region 264 of device 250, plate region 270 being held down by the individual's weight.

When stump 252 is then released, the stretched hip muscle fibers and connective tissue contract and pull the stump and flex first thigh region 264 back toward LROM angle $\alpha_0$. As a result, thigh region 262 of device plate 256 becomes temporarily flexed or elastically bent into a curve in the same manner that a limb of an archery bow is flexed and bent when the bow is drawn to shoot an arrow. As stump 252 is thus pulled back against the bending of thigh region 262 and approaches LROM angle $\alpha_0$, the associated hip muscles and connecting tissue relax to an extent that energy stored in the flexed thigh region 252 of plate 256, pulls stump 252 back toward ROM angular position $\alpha_1$ against the restoring forces of the hip muscle fibers and connecting tissue.

After a number of such cycles (as depicted in FIG. 3), the angular ROM of stump 252 is extended to angle $\alpha_1$. At this point, device 250 is removed from the individual and the stump is massaged to a further extended ROM angle $\alpha_2$ and is held there while plate 256 is heated along line 268 and is bent to new ROM angle $\alpha_2$. Device 250 is reapplied to the individual as described above and the just-described cycling procedure is repeated until the angular ROM of stump 252 has increased to angle $\alpha_2$. This procedure is repeated until the full angular ROM (for example, angle $\alpha_4$) is achieved.

From the foregoing description, it can be seen that device 250 is exactly analogous to devices 140 and 200 which have been described above. In the case of device 250, the material of plate portion 256 adjacent bend line 268 deforms in operation, for example, like hinges 170 and 178 described initially in connection with device 140.

Figure 16:
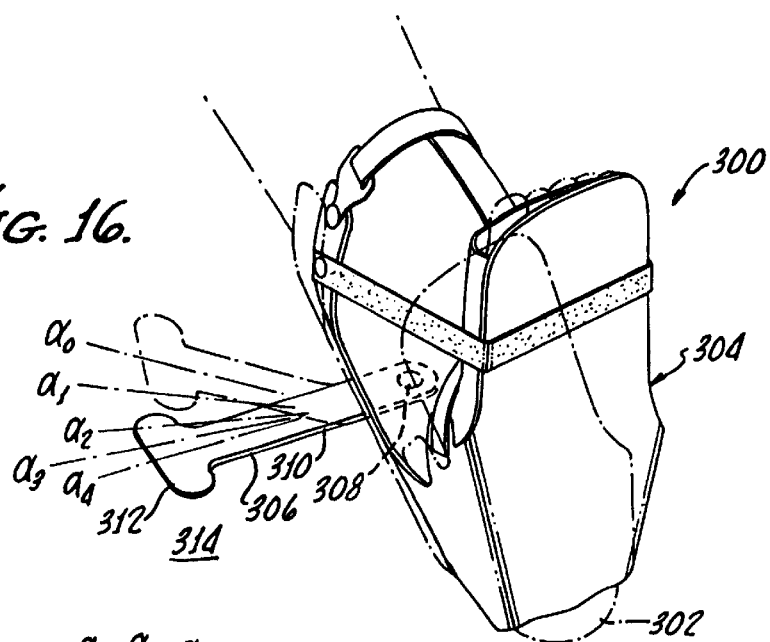
FIG. 16 is a perspective drawing of a foot-type orthotic device in accordance with the present invention for treating contracture of a foot with the toe pointing inwardly and showing construction of the device, including boot and bar portions and showing the boot attached to an individual's foot.

Foot-Type Orthotic Device of FIG. 16:

There is depicted in FIG. 16 a foot-type orthotic device 300 in accordance with the present invention for therapeutic treatment of inversion of the foot, and external rotation of the hip. By way of example, FIG. 16 depicts in phantom lines a foot 302 that as a result of contracture is turned inwardly(inversion).

Comprising device 300 are a boot portion 304, to a rearward region of which is attached a plastic bar 308. Bar 308 may be constructed of the same plastic material as plate 256 of stump-device 250 described above and has a bend line 310.

With partial boot 304 installed on an individual's foot 302 and the individual resting on a surface, such as a bench, the floor or a bed(designated by reference number 314), an end region 312 of bar 306 bears against the floor, bench or bed.

Through a sequence of therapeutic foot extension steps in which bar 306 is heated and bent at angles $\alpha_1$ through $\alpha_4$ at bend line 310, associated with a like sequence of increasing foot ROM angular positions from contracture LROM angle $\alpha_0$ to fully extended ROM angle $\alpha_4$, a full ROM of the foot is achieved in precisely the same manner described above for stump-type device 250. Accordingly, no further description of foot-type orthotic device 300 is considered necessary.

Figure 17:
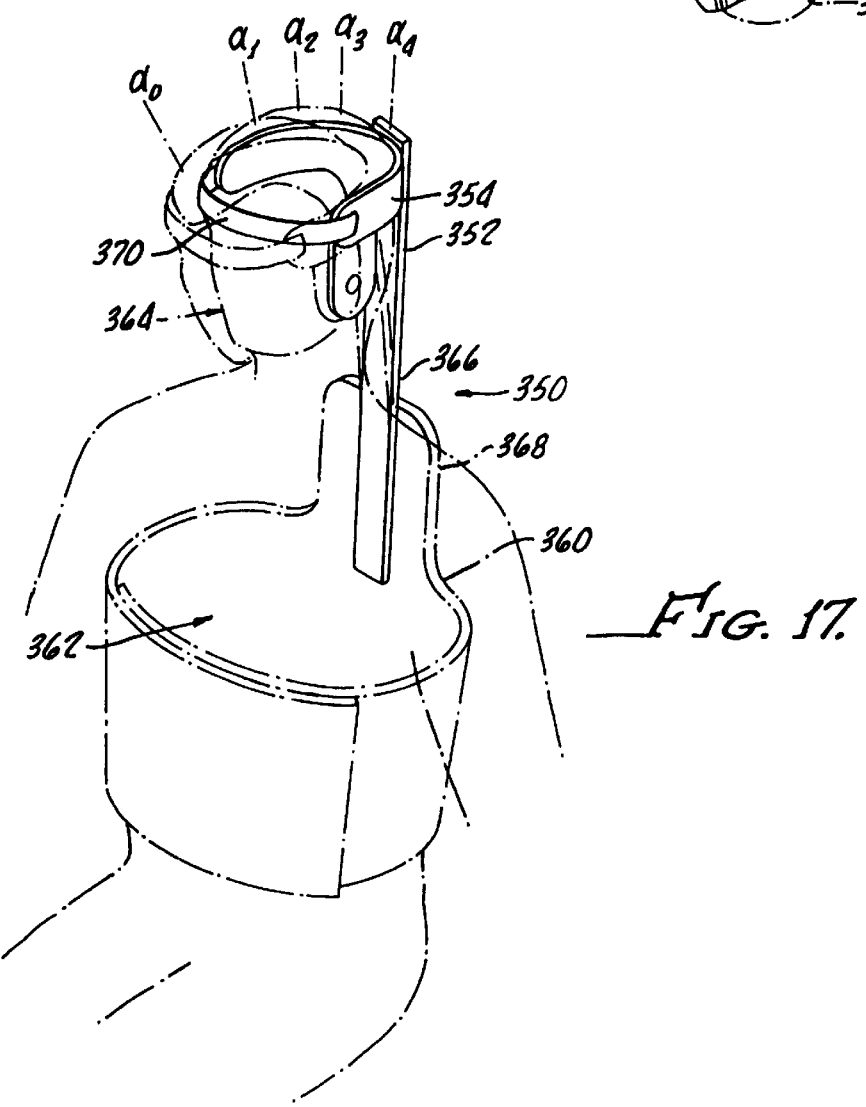
FIG. 17 is a perspective drawing of a first neck/head positioning-type orthotic device in accordance with the present invention for treating contracture of the cervical region of the spine (neck)with the head in a forward and downward direction by contracture of neck muscle fibers and connective tissue showing an elongated neck plate having attached to upper regions thereof a headband for detachably attaching to an individual's head and further showing an upper torso encircling member for retaining lower regions of the neck plate.

Cervical Extension Orthotic Device of FIG. 17:

A forward cervical extension orthotic device 350 depicted in FIG. 17 is similar in general construction and operation to stump-type device 250 and foot-type device 300 described above. Comprising cervical extension orthotic device 350 is a cervical extension flexible bar or stem 352, which is preferably constructed of the same flexible plastic material as plate 256. A head-restraining member or headpiece 354 is attached to an upper end of stem 352. A lower region of stem 352 is retained inside a vest-like retainer 360 that is detachably attached (as by hook and loop fasteners) around an upper body portion 362 of the individual being therapeutically treated by device 350.

With the individual's head 364 initially bent sharply forwardly and downwardly at a LROM angular position $\alpha_0$, due to contracture of neck muscle fibers and connecting tissue, the head is massaged upwardly and backwardly to ROM angular position $\alpha_1$ and is held in that position.

After the head angle $\alpha_1$ has been measured (for example, by a goniometer), device stem 352 is heated along a transverse bend line 366 to a matching angle. A lower end region of stem 352 is then inserted downwardly into an upper region 368 of retainer 362. Headpiece 354 is detachably attached by a strap 370 around head 364 and the head is released.

As described below, for example, relative to stump-type device 250 (FIGS. 14 and 15), head 364 is released and is pulled by contracted muscle fibers and connective tissue back toward LROM angle $\alpha_0$, thereby flexing stem 352, which then pulls the head back towards angle $\alpha_1$—all in the manner described above. This cycle is repeated until the head's ROM has been extended to ROM angle $\alpha_1$.

Headpiece 354 is then detached from head 364 and device 350 is detached from the individual. Head 364 is then massaged to angular position $\alpha_2$ and is held there while stem 362 is reheated and rebent at bend line 366 to a matching angle, at which time device 350 is reinstalled on the individual as depicted in FIG. 17. When head ROM position $\alpha_2$ has been established in the manner for ROM angular position $\alpha_1$ p, the operation is repeated as many times as is required to fully extend the ROM of head 364, for example, at ROM angle $\alpha_4$.

Figure 18:
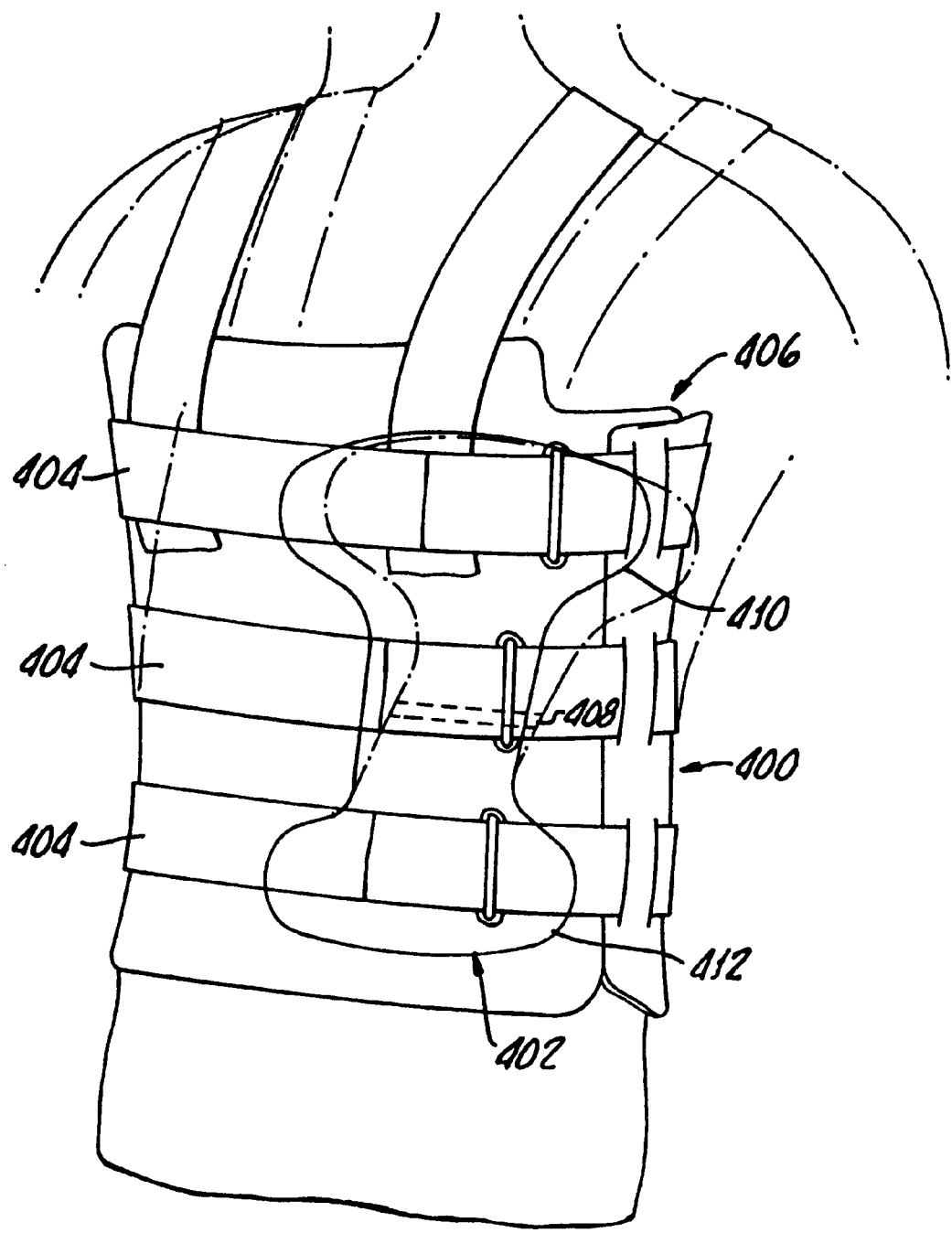
FIG. 18 is a perspective drawing of a back-type orthotic device in accordance with the present invention for treating a non-functional functional (forward, backward, S-shaped curvature of an individual's spine and showing a back plate and upper and lower regions of an upper torso harness for detachably attaching corresponding upper and lower regions of the device to an individual.

Back-Type Orthotic Device of FIG. 18:

There is shown in FIG. 18 a back-type orthotic device 400 according to the present invention which is useful for extending the ROM of an individual's back which is involuntarily restricted by contracture of back muscle fibers and connective tissue to an LROM which misshapes the individual's back, for example, into a general S-shape.

Comprising orthotic device 400 are a generally I-shaped flexible plate 402 (which is preferably constructed of the same material as plate 256 of stump-type orthotic device 250) and a harness assembly 404 which is worn around the upper torso 406 for detachably attaching the back plate to the individual's back in the region of contracture. A transverse bend line 408, which functions as a lockable hinge, separates plate 402 into respective upper and lower portions 410 and 412.

Back plate 400 functions and is operated in conjunction with the individual's back in the same manner that stump device plate 256 and device stem 352 of cervical extension orthotic device 350 as the ROM of the individual's back is increased from an initial LROM angle $\alpha_0$ to a fully extended (that is, straightened) ROM angle, for example angle $\alpha_4$. In the above-described manner, for example, for orthotic device 350. During such procedure, back plate 402 is heated and bent along bend line 408 at each increased ROM angle of the individual's back (for example, at ROM angles $\alpha_1$, $\alpha_2$, $\alpha_3$ and $\alpha_4$. In each case, the flexing of plate 402 about bend line 408 working against contracture forces of the individual's back causing a cycling between angles $\alpha_0$ and $\alpha_1$, between $\alpha_1$ and $\alpha_2$ and so forth in the manner described above until the full ROM of the back I attained.

Upper Torso-Type Orthotic Device of FIG. 19:

There is shown in FIG. 19 an upper torso-type orthotic device 450 in accordance with the present invention for treating sideways or forward contracture of an individual's upper torso relative to the individual's lower torso, and for restoring the full side-to-side and forward-to-straight ROM of the upper torso.

Comprising device 450 are a member 452, which is preferably constructed of the same flexible plastic material as, for example, plate 256 described above, and strap means 454 for detachably attaching the member to an individual's upper torso and thighs, as depicted in FIG. 19 and as described below.

Member 452 is formed in one piece of right and left side L-shaped side portions 456 and 458, respectively, which fit vertically along the individual's right and left sides and horizontally along the seated individual's respective right and left thighs 460 and 462. Further comprising member 452 is an arcuate portion 464 which interconnects upper end regions of side portions 456 and 458, and which fits around forward regions of the individual's upper torso. Member 452 is preferably padded to provide comfort to the individual.

Vertical sections or regions of side portions 456 and 458 function in the manner of stem 352 of orthotic device 350, as described above in connection with FIG. 17. In that regard, each of the vertical sections of side portions 456 and 458 have transverse bend lines 470 and 472, respectively, which divide the vertical sections into upper and lower regions and which function in the manner of lockable hinges interconnecting such upper and lower regions.

In the manner described above, for example, in conjunction with stump-type orthotic device 250 (FIGS. 14 and 15) and cervical extension orthotic device 350 (FIG. 17), the individual's upper torso is worked from an initial LROM angular position $\alpha_0$ caused by contracture, through increasing greater ROM angular positions $\alpha_1$, $\alpha_2$ and $\alpha_3$ until the full ROM angular position $\alpha_4$ is reached (it is, of course to be understood that more or fewer than the four ROM angular positions $\alpha_1$, $\alpha_2$, $\alpha_3$ and $\alpha_4$ may, in practice, be required).

Further in the manner described above relative to orthotic devices 250, 300, 350 and 400, these ROM angular positions $\alpha_1$, $\alpha_2$, $\alpha_3$ and $\alpha_4$ of the individual's torso are provided by sequentially bending vertical sections of side portions 456 and 458 about respective bend lines 470 and 472 at angles $\alpha_1$, $\alpha_2$, $\alpha_3$ and $\alpha_4$, the side sections being elastically bent at each ROM angular position by contractive forces of the torso pulling the torso back toward the previous ROM angular position.

Ankle-Type Orthotic Device of FIG. 20:

There is depicted in FIG. 20 an ankle-type orthotic device 500 further in accordance with the present invention, that is configured for treating contracture of an individual's foot 502 relative to the individual's lower leg 504, about the ankle 506. The particular type of contracture depicted is such that foot 502 is straightened out or is in a "footdropped" condition, with its LROM angular position at $\alpha_0$. Other types of contracture of foot 502 are possible and are therapeutically treated in a manner similar to that described hereinbelow for the dropped-foot condition.

Device 500 comprises a single piece slipper-shaped flexible plastic member 508 which has sole and ankle regions 510 and 512, respectively. Preferably, a cutout 514 is provided in member 508 at heel 506 to eliminate pressure on the heel. A transverse bend line is located along a transverse axis 516 through cutout 514. A soft inner padding 518 is provided which wraps about foot in a protective manner. Included in orthotic device 500 is a detachable strap 520 for holding the device 500 onto foot 502.

Right and left side adjustable side straps 522 and 524, respectively, are connected to an upper end of ankle region 512 by a back-strap 526 and extend under sole region 510 for enabling alignment of foot 502 as may be necessary.

Member 508, which is constructed from a flexible, thermal-setting plastic, is successively bent around bend axis 516 at angles $\alpha_1$, $\alpha_2$, $\alpha_3$ and $\alpha_4$ to extend the angular ROM of foot 502 from its LROM position of $\alpha_1$ to its full ROM of $\alpha_4$ in the same manner described above for orthotic devices 250, 300, 350, 400 and 450. Consequently, a further detailed description of orthotic device 500 is not considered to be necessary, except to note that single piece member 598 may alternatively be constructed of two separate sections corresponding to sections 510 and 512 which are interconnected with interconnection members similar to above-described members 160 and 162 of orthotic device 140 (FIGS. 5–8).

Figure 21:
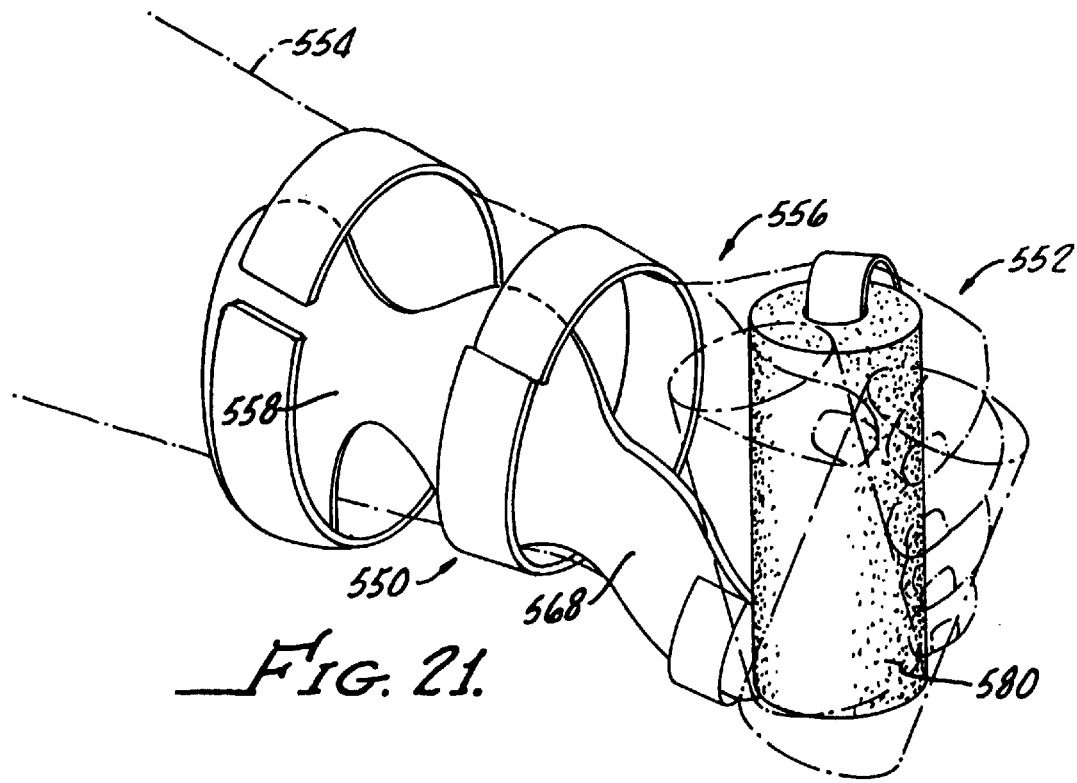
FIG. 21 is a perspective drawing of a wrist-hand-finger-type orthotic device in accordance with the present invention showing the manner in which the device is constructed and detachably attached to an individual's wrist for treating contracture of an individual's hand relative to his or her wrist, and showing how the device may be used for treatment of contracture of the individual's fingers relative to his or her hand.
Figure 22:
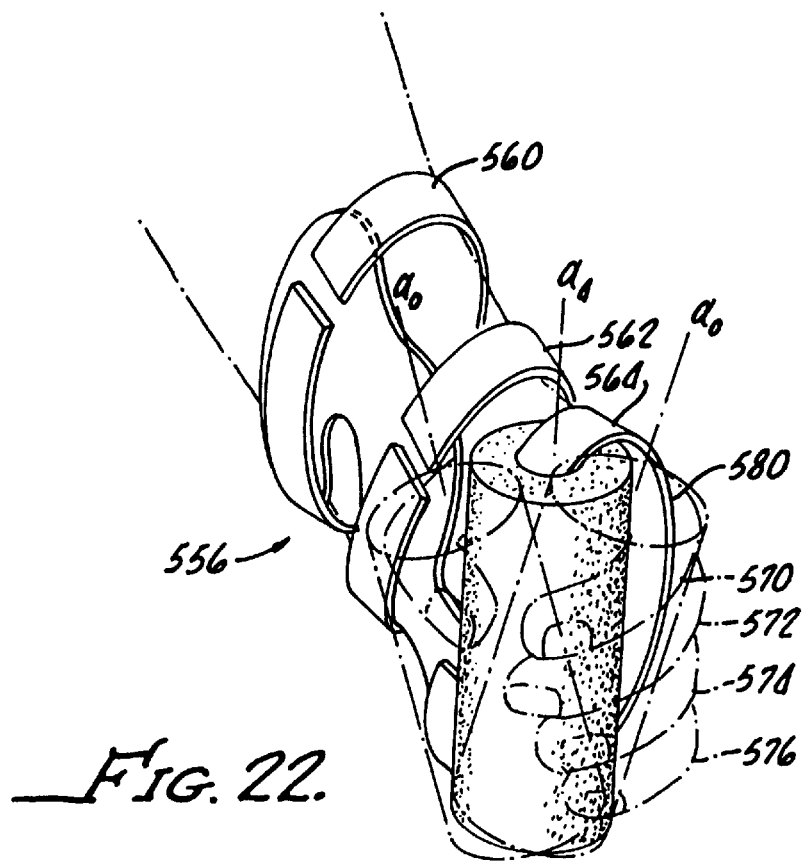
FIG. 22 is a perspective drawing of the wrist-hand-finger-type orthotic device depicted in FIG. 14, showing the manner in which the device is used for treating contracture of the individual's hand relative to his or her wrist and also showing how the device may be used for treatment of contracture of the individual's fingers relative to his or her hand, and further showing the manner in which graduated small-to-large finger rolls can be attached to the orthotic device for treatment of contracture of the fingers.

Wrist-Type Orthotic Device of FIGS. 21 and 22:

There is shown in FIGS. 21 and 22 a wrist-type orthotic device 550 in accordance with the present invention for treating one or more types of contracture afflicting an individual's hand 552 relative to forearm 554 about a wrist 556. Shown comprising orthotic device 550 are an elongate, flexible plastic member 558 which is fashioned to fit the inner surface shape of an individual's lower forearm 554, wrist 556 and palm of his or her hand 552. Included in device 550 are adjustable straps: forearm strap 560, wrist strap 562 and hand strap 564.

It can be understood that a healthy individual can rotate his or her hand 552 through a complete circle relative to forearm 554 about wrist connection or joint 556. For orthotic device 550, member 558 is shaped and bent at any appropriate bend or torsion line, for example, transverse bend line 568( FIG. 21), to treat different various contractures affecting hand 552 with respect to forearm 554.

Consequently, applied to present orthotic device 500 for treating contractures of hand 502 is the same method described above with respect to orthotic devices 250, 300, 350, 400 and 450, including bending the associated flexible plastic members 256, 310, 352, 402, 452 in incremental, progressive angular steps to increase the ROM of an affected body part from its LROM of $\alpha_0$, through intermediate ROM angles $\alpha_1$, $\alpha_2$ and $\alpha_3$, to the fully extended ROM angle $\alpha_4$.

Shown also in FIGS. 21 and 22 with respect to orthotic device 500 are means 570 for treating contracture of fingers 570, 572, 574 and 576 by means of a flexible cylinder 580, as more particularly described with respect to the following head-type orthotic device.

Figure 23:
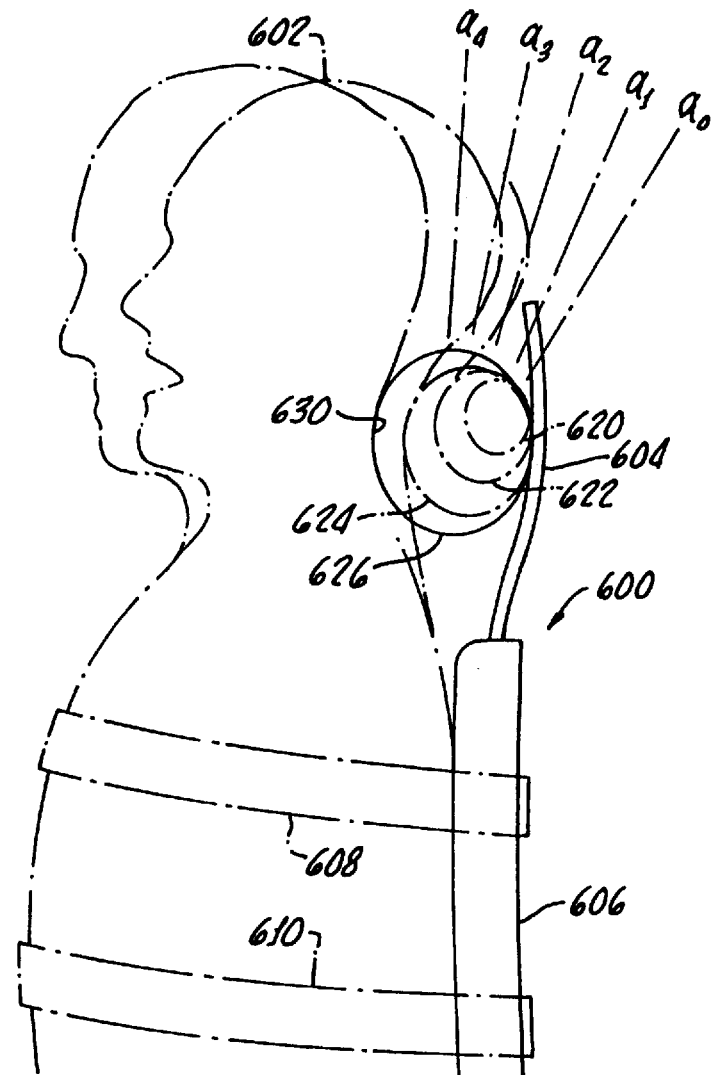
FIG. 23 is a side view of a head back type of orthotic device in accordance with the present invention for treating contracture of an individual's neck in a backwardly bent LROM angular contracture position, showing an upwardly-extending back member, means for detachably attaching lower regions of the back plate to an individual's upper body and a elastomeric neck cylinder disposed between upper regions of the back plate and the back of the individual's neck just below the individual's head.
Figure 24:
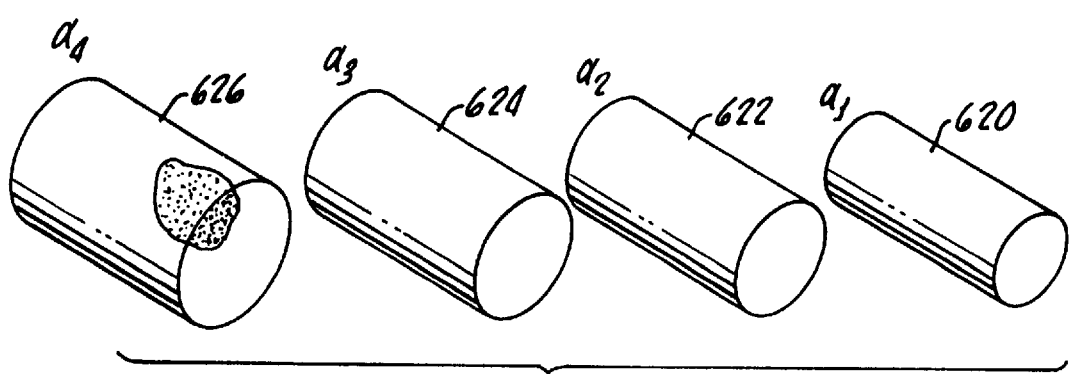
FIG. 24 is a perspective drawing showing a series of neck cylinders of graduated diameter useful in the head backward orthotic device of FIG. 23 (and which are representative of the finger rolls used in the hand-type orthotic device of FIG. 22)

Head Hyperextension-Type Orthotic Device of FIGS. 23 and 24:

Shown in FIGS. 23 and 24 is a hyperextension-type orthotic device 600, in still further accordance with the present invention, for treating a contracture of neck muscular fibers and connecting tissue which causes an individual's head 602 to be involuntarily held in an extreme head-back LROM angular position $\alpha_0$ (FIG. 23).

Comprising orthotic device 600 is a slightly curved stiff bar 604, a lower end region of which is retained in a block 606 that is detachably held to the individual's back by adjustable straps 608 and 610. Further comprising orthotic device 600 is a series of elastic cylinders or neck bolsters 620, 622, 624 and 626 (FIG. 24 and shown in phantom line in FIG. 23). These bolsters 620, 622, 624 and 626 have respective diameters which correspond to progressively greater ROM angles $\alpha_1$, $\alpha_2$, $\alpha_3$ and $\alpha_4$, and when are sequentially installed between bar 604 and a back region 630 of the individual's head cause the head to be moved to corresponding ROM angular positions $\alpha_1$, $\alpha_2$, $\alpha_3$ and $\alpha_4$ from contracture LROM position $\alpha_0$, to ROM angular positions $\alpha_1$, $\alpha_2$, $\alpha_3$ and $\alpha_4$ in the same manner that would occur if bar 504 were to be progressively bent to such ROM angles (in the manner described above for orthotic devices 250, 300, 350, 400, 450, 500 and 550).

This principle of using cylinders or bolsters of increasing diameters is used as well to treat contracture of an individuals fingers 570, 572, 574 and 576 for orthotic device 550 (FIGS. 21 and 22).

Figure 25:
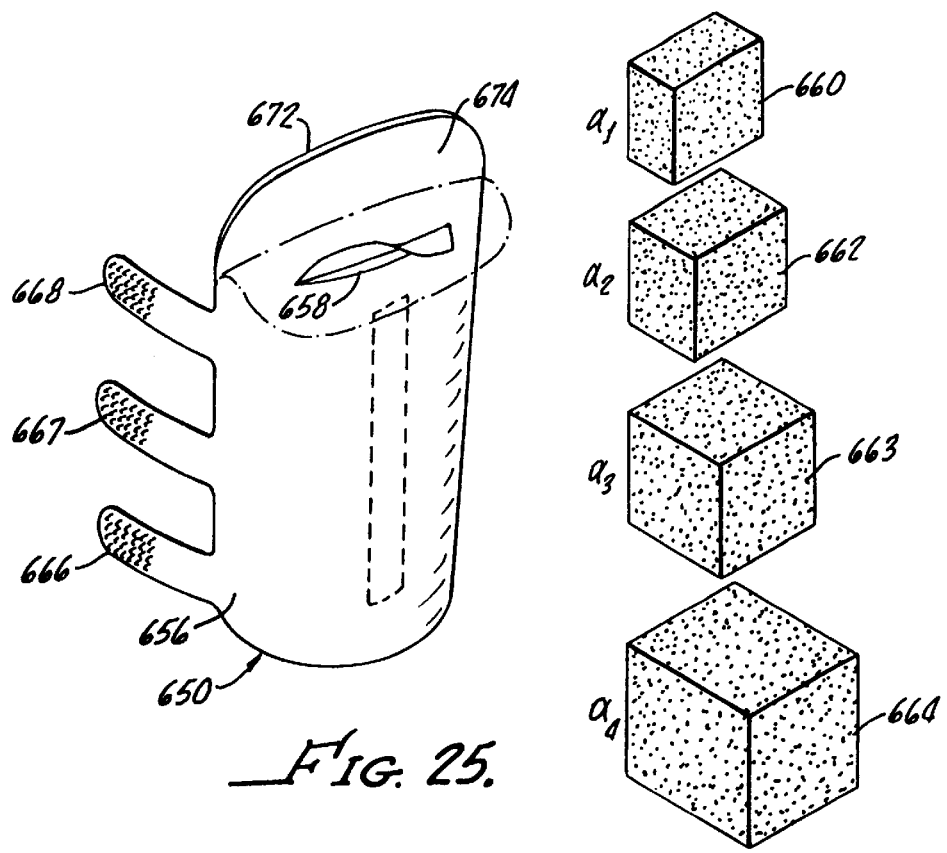
FIG. 25 is a perspective drawing of a shoulder-type orthotic device further in accordance with the present invention for treating a contracture of an individual's arm relative to the individual's upper body in which the upper arm has a LROM relative to the upper body, showing construction of the device having a pocket for receiving and holding various sizes of elastomeric blocks for causing progressively-increasing ROM of the arm.
Figure 26:
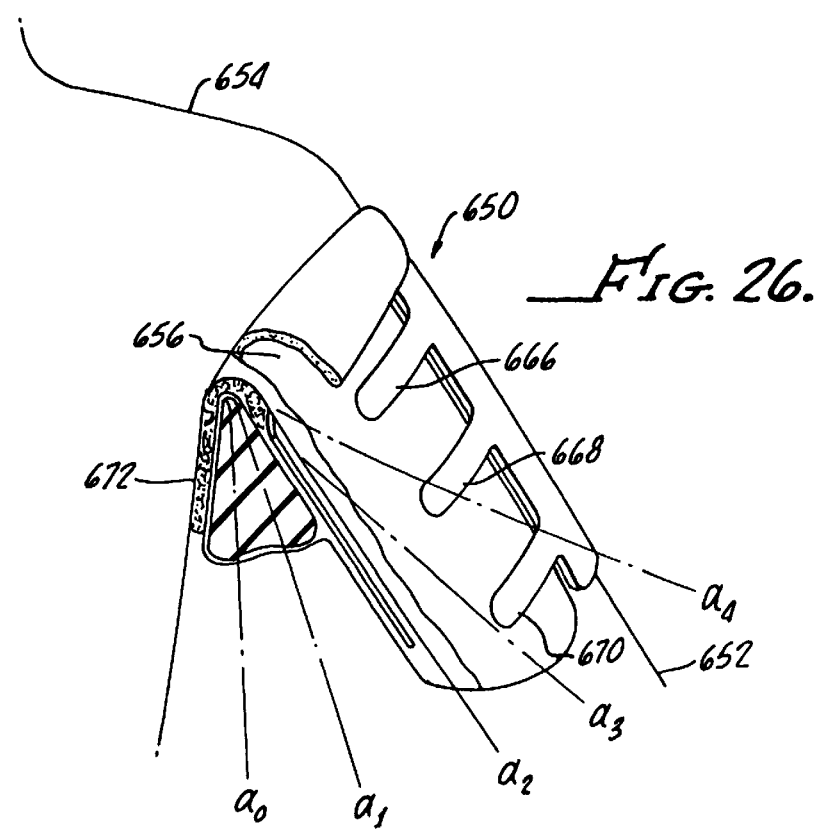
FIG. 26 is a perspective drawing of the shoulder-type orthotic device of FIG. 25 showing the manner in which the device is detachably attached to the individual's upper arm.

Shoulder- and Arm-Type Orthotic Device of FIGS. 25 and 26:

There is shown in FIGS. 25 and 26 a shoulder-and arm-type orthotic device 650, in accordance with the present invention, whish is used to treat contracture of an individual's arm 652 relative to the individual's shoulder 654 (FIG. 26). Shown comprising orthotic device 650 are a flexible pillow body 656 having an internal recess or pocket 658 for receiving one of graduated flexible plastic elements 660, 662, 664 and 666 which are sized and or otherwise constructed (for example, of increasingly denser or stiffer materials) to correspond to progressively greater ROM angles $\alpha_1$, $\alpha_2$, $\alpha_3$ and $\alpha_4$ of arm 652 relative to shoulder 654.

In operation, after arm 652 has been extended from LROM angle $\alpha_0$ relative to shoulder 654, by manual massage and slow extension, to ROM angular position $\alpha_1$, and the arm is held in that angular position, elastic element 660 (which corresponds to ROM angle $\alpha_1$) is inserted into pocket 658. Thereafter, body 656 (which is constructed of a pliable material, such as nylon fabric) of orthotic device 650 is detachably attached to under regions of arm 652, in the individual's armpit, by adjustable straps 666, 668 and 670, with a body flap 672 abutting the individual's body (FIG. 26). In this case, the intersection line 674 between body 656 and flap 672 functions as a hinge and element 660 functions as a hinge lock.

In such attachment of orthotic device 650, elastic element 660 functions as a spring which is unloaded at ROM angle $\alpha_1$. When the individual's arm 652 is then released, the contracture of muscle fibers and connecting tissue in the armpit region pulls the arm back toward LROM angular position $\alpha_0$, thereby compressing element 660.

This compression of element 660 counteracts the contracture and, when the muscle fibers and connective tissue relax or fatigue, pushes arm 652 back away from the individual's body toward ROM angular position $\alpha_1$. After several or a number of such contraction and extension cycles, arm 652 achieves the extended ROM of $\alpha_1$.

The foregoing procedure is repeated, using elastic elements 662, 664 and 666 (through intermediate ROM angular positions $\alpha_2$ and $\alpha_3$) until arm 652 reaches its fully extended ROM angular position $\alpha_4$.

From the foregoing description, it will be appreciated that orthotic device 650 functions in the same manner, for example, as elbow-type orthotic device 140 (Ref. FIGS. 5–11) and knee-type orthotic device 200 (Ref. FIG. 12) described above, with elastic elements 660, 662, 664 and 664 taking the place of spring-type connecting members 160 and 162 (for device 140) and 160*b* and 162*b* (for device 200). In fact, orthotic device 650 can be modified in an obvious mariner to serve as orthotic devices for treating contracture of the elbow and contracture of the knee.

Figure 27:
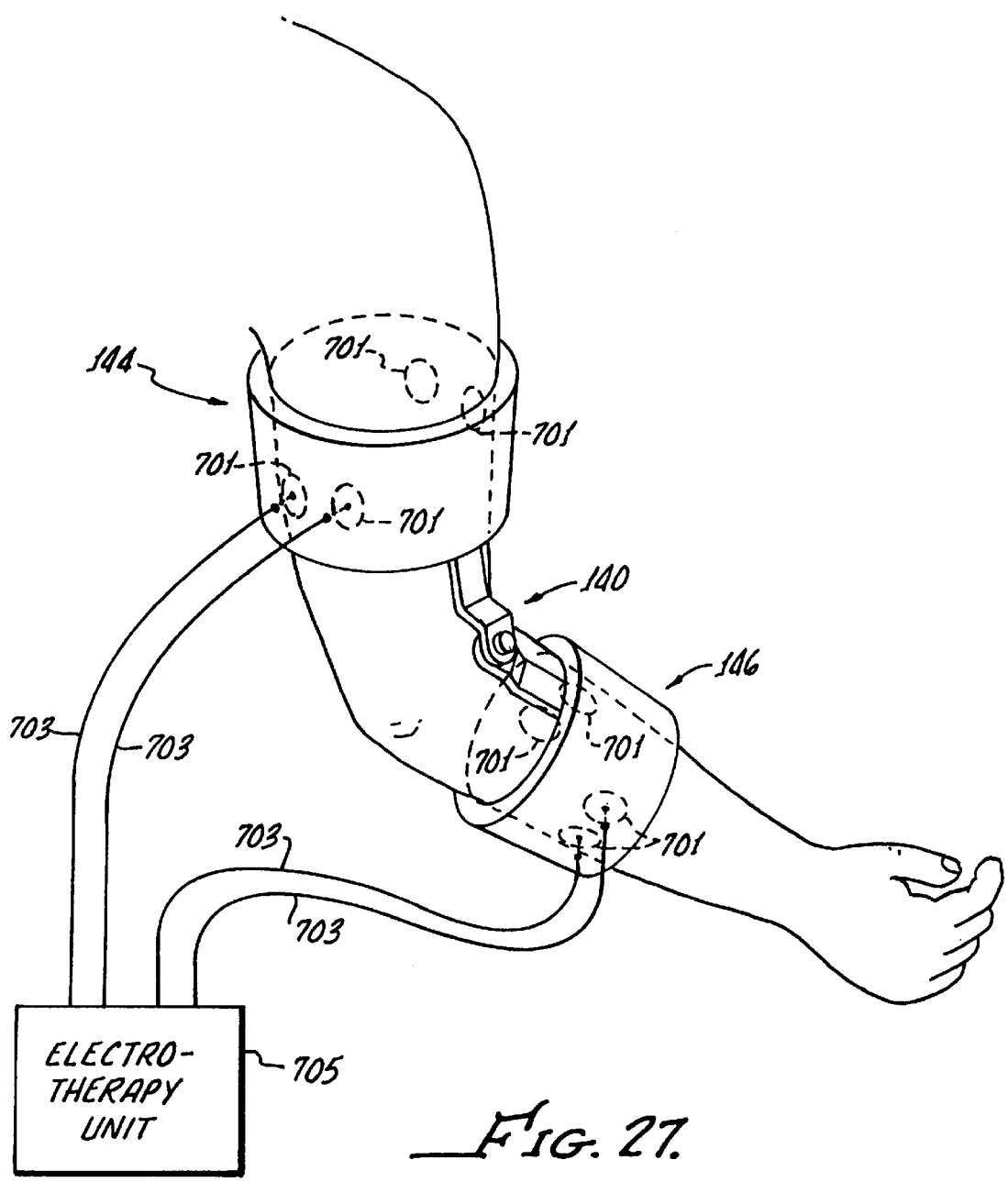
FIG. 27 is a perspective drawing of an elbow-type orthotic device in combination with an electrode component and an electrotherapy unit.

FIG. 27 illustrates one embodiment combining orthotic therapy and electrotherapy. Individual electrodes 701 are located on upper arm member 144 and lower arm member 146 of elbow-type orthotic device 140.

The electrodes 701 are of any suitable structure and are made of electrically conductive material. For example, electrodes 701 may be made of electro-mesh material which is sewn to the soft parts of orthotic device 140. Alternately, electrodes 701 may be conventional peel and stick electrodes, for example, peel and stick gel adhesive electrodes, which are stuck onto the soft parts of orthotic device 140. The electrodes 701 are positioned to be in close proximity to, preferably directly adjacent, the body parts being treated. Each of the electrodes 701 is adapted to be detachably connected to one of the electric wires 703, for example, using any suitable connector many of which are conventional and well known in the art. Many electrode connection appliances are available, for example, wire plug connections, snap on wires, electrical signal transmitter to receptor electrode connections, and others. Also, the number of electrodes can vary widely, for example, in a range of about 2 to about 4 or about 8 or about 16 or more per orthotic device.

Electrodes 701 in proximity to the extensor muscles of the arm in FIG. 27 are connected by electric wires 703 to electrotherapy unit 705, which may be of conventional design. Electrodes 701 in proximity to the flexor muscles of the arm are not connected to the electrotherapy unit 705. However, if desired, the wires 703 can be disconnected from the "extensor muscle" electrodes 701 and connected to the "flexor muscle" electrodes. Other combinations of electrodes 701 can be connected to unit 705 to achieve a desired treatment. For example, if it is desired to pass electric current through the elbow joint, preferably the polarity of the power being passed through the electric wires 703 to the electrodes 701 on upper arm member 144 is reversed relative to the polarity of the power being passed to the electrodes 701 on lower arm member 146. This approach provides an "X" pattern of electric current through the elbow which is particularly therapeutically effective.

The electrotherapy unit 705 can be either attached to the orthotic device 140 or simply connected to the orthotic via electrode connections. The electrotherapy unit 705 may be portable, for example, suitable for being carried on the body of the patient being treated. Also, the unit 705 may be powered by line voltage, suitably transformed down to an acceptably reduced voltage, or may be powered using one or more storage batteries, for example, of conventional design.

The electrodes 701, wires 703 and electrotherapy unit 705 are used to conduct electrical current to the elbow and related muscles, tendons, and connective tissue on or near which device 140 is located.

Soft tissue electrotherapy, microcurrent electrotherapy, nerve stimulation or high volt therapy could be provided as needed to treat joint related problems. Enhanced muscle and tendon stretch can be achieved by placing electrodes (connected to an electrotherapy unit) at the location of the contracted muscles. Antagonist muscle groups can be stimulated to provide muscle strengthening and re-education on a different or same setting of the electrotherapy unit.

It is to be understood that although for descriptive purposes, extension of a skeletal body part, such as a forearm, foot, lower leg, head, hand, and the like has been described in terms of extension to a extended range of motion (EROM) from an initial limited range of motion (LROM) angle $\alpha_0$ to an extended angle $\alpha_4$ through intermediate ROM angular positions $\alpha_1$, $\alpha_2$ and $\alpha_3$, it is to be understood that no limitation is intended or implied thereby. In actual practice, a greater or lesser number of intermediate ROM angles may be required. Moreover, the number of degrees between each adjacent pair of ROM angular positions will usually not be equal.

It is also to be understood that although several different configurations of orthotic devices have been described, all function according to the same principle—that of the contracture forces loading a spring to thereby cause a return to an extended ROM.

Although there has been described and illustrated various types of orthotic devices utilizing the same principle for treating contractures of various parts of a human body in accordance with the present invention for purposes of illustrating the manner in which the invention may be used to advantage, it is to be appreciated that the invention is not limited thereto. Therefore, any and all variations and modifications that may occur to those skilled in the applicable art are to be considered as being within the scope and spirit of the claims as appended hereto.

I claim:

1. An orthotic device useful for extending the range of angular movement between adjacent first and second skeletal body parts which have been drawn to and involuntarily held in a limited angular range of motion (LROM) position relative to one another by contraction of muscle fibers and connective tissue due to immobility of one or both of said skeletal body parts, said orthotic device comprising:

a. a thermal setting, flexible member having first and second regions;

b. a bend line between said first and second member regions, a bend at said bend line being set by heating, bending and cooling said member at said bend line, said bend line permitting angular movement and enabling the setting of a selected angle between said first and second member regions;

c. means for applying or attaching said first member region to said first body part and said second orthotic device portion to said second body part after the second body part has been moved against contracture forces away from said LROM position to an initial extended range of motion (EROM) angular position relative to said first body part, said first and second member regions being then set at said initial extended range of motion position relative to one another;

d. spring means associated with said first and second member regions for urging said second member region to return to said EROM position in response to the second member region being pulled by the applied or attached first body part through at least one of muscle fiber contraction and the elastic properties of the muscle fibers and connective tissue away from said EROM position and toward said LROM position, thereby causing a cycling movement of said second body part between said EROM and said LROM angular positions and a gradual loosening of said second body part relative to said first body part and an ultimate extending of the range of angular motion of said second body part relative to said first body part at said EROM position without additional external intervention; and e. an electrode component positioned to be effective to conduct an electrical current to at least one of said body parts.

2. The orthotic device as claimed in claim 1, which further comprises an electrotherapy unit in electrical communication with said electrode component.

3. The orthotic device as claimed in claim 1 wherein said electrode component comprises a plurality of individual electrodes.

4. The orthotic device as claimed in claim 1 wherein said electrode component includes peel and stick gel adhesive electrodes.

5. The orthotic device as claimed in claim 1 wherein said electrode component comprises electrically conductive material.

6. The orthotic device as claimed in claim 1 wherein said electrode component comprises electro-mesh material.

* * * * *